(12) United States Patent
Chesnin

(10) Patent No.: US 11,491,303 B2
(45) Date of Patent: Nov. 8, 2022

(54) MEDICAL TUBE CLEARANCE DEVICE

(71) Applicant: ClearFlow, Inc., Irvine, CA (US)

(72) Inventor: Kenneth Chesnin, Long Beach, CA (US)

(73) Assignee: CLEARFLOW, INC., Irvine, CA (US)

(*) Notice: Subject to any disclaimer, the term of this patent is extended or adjusted under 35 U.S.C. 154(b) by 0 days.

(21) Appl. No.: 17/528,454

(22) Filed: Nov. 17, 2021

(65) Prior Publication Data

US 2022/0152342 A1 May 19, 2022

Related U.S. Application Data

(60) Provisional application No. 63/114,843, filed on Nov. 17, 2020.

(51) Int. Cl.
*A61B 90/70* (2016.01)
*B08B 9/04* (2006.01)
*A61M 25/00* (2006.01)

(52) U.S. Cl.
CPC ............. *A61M 25/00* (2013.01); *A61B 90/70* (2016.02); *B08B 9/04* (2013.01); *A61B 2090/701* (2016.02); *A61M 2025/0019* (2013.01); *A61M 2205/0272* (2013.01); *B08B 2209/04* (2013.01)

(58) Field of Classification Search
CPC ............. A61B 90/70; A61B 2090/701; A61M 2025/0019; A61M 2205/0272; B08B 9/04; B08B 2209/04
See application file for complete search history.

(56) References Cited

U.S. PATENT DOCUMENTS

| | | | |
|---|---|---|---|
| 3,416,532 A | 12/1968 | Grossman |
| 3,946,741 A | 3/1976 | Adair |
| 3,957,054 A | 5/1976 | McFarlane |
| 3,991,762 A | 11/1976 | Radford |
| 4,006,743 A | 2/1977 | Kowarski |
| 4,056,104 A | 11/1977 | Jaffe |
| 4,148,319 A | 4/1979 | Kasper et al. |
| 4,228,802 A | 10/1980 | Trott |
| 4,257,422 A | 3/1981 | Duncan |
| 4,317,452 A | 3/1982 | Russo et al. |
| 4,324,262 A | 4/1982 | Hall |

(Continued)

FOREIGN PATENT DOCUMENTS

| | | |
|---|---|---|
| DE | 68906380 T2 | 1/1994 |
| DE | 102004013712 B3 | 8/2005 |

(Continued)

OTHER PUBLICATIONS

International Search Report & Written Opinion issued in PCT/US2021/059687 dated Mar. 4, 2022, 14 pages.

*Primary Examiner* — Natasha N Campbell
(74) *Attorney, Agent, or Firm* — Pearne & Gordon LLP

(57) ABSTRACT

Methods and devices for actuating a clearance device to clear obstructive debris from medical tubes are disclosed. More particularly, a shuttle that includes a first primary magnetic element that is adapted to magnetically engage and translate a magnetic guide within a tube is disclosed. The first primary magnetic element is aligned so that a first primary magnetic field emanating therefrom is aligned substantially perpendicular to a longitudinal axis of the tube when viewed from a side of the shuttle.

23 Claims, 15 Drawing Sheets

(56) References Cited

U.S. PATENT DOCUMENTS

| | | |
|---|---|---|
| 4,429,693 A | 2/1984 | Blake et al. |
| 4,445,897 A | 5/1984 | Ekbladh et al. |
| 4,465,481 A | 8/1984 | Blake |
| 4,523,920 A | 6/1985 | Russo |
| 4,569,344 A | 2/1986 | Palmer |
| 4,638,539 A | 1/1987 | Palmer |
| 4,692,153 A | 9/1987 | Berlin et al. |
| 4,696,296 A | 9/1987 | Palmer |
| 4,698,058 A | 10/1987 | Greenfeld et al. |
| 4,706,671 A | 11/1987 | Weinrib |
| 4,723,549 A | 2/1988 | Wholey et al. |
| 4,728,319 A | 3/1988 | Masch |
| 4,762,125 A | 8/1988 | Leiman et al. |
| 4,771,772 A | 9/1988 | DeWitt |
| 4,781,678 A | 11/1988 | de Couet et al. |
| 4,865,030 A | 9/1989 | Polyak |
| 4,865,586 A | 9/1989 | Hedberg |
| 4,889,106 A | 12/1989 | Watanabe |
| 4,909,781 A | 3/1990 | Husted |
| 4,921,488 A | 5/1990 | Maitz et al. |
| 4,950,232 A | 8/1990 | Ruzicka et al. |
| 4,967,743 A | 11/1990 | Lambert |
| 5,003,657 A | 4/1991 | Boiteau et al. |
| 5,009,659 A | 4/1991 | Hamlin et al. |
| 5,062,835 A | 11/1991 | Maitz et al. |
| 5,073,164 A | 12/1991 | Hollister et al. |
| 5,141,503 A | 8/1992 | Sewell, Jr. |
| 5,188,618 A | 2/1993 | Thomas |
| 5,215,522 A | 6/1993 | Page et al. |
| 5,240,675 A | 8/1993 | Wilk et al. |
| 5,260,020 A | 11/1993 | Wilk et al. |
| 5,261,877 A | 11/1993 | Fine et al. |
| 5,297,310 A | 3/1994 | Cox et al. |
| 5,336,177 A | 8/1994 | Marcus |
| 5,349,950 A | 9/1994 | Ulrich et al. |
| 5,370,610 A | 12/1994 | Reynolds |
| 5,490,503 A | 2/1996 | Hollister |
| 5,505,713 A | 4/1996 | Van Antwerp |
| 5,514,112 A | 5/1996 | Chu et al. |
| 5,520,635 A | 5/1996 | Gelbfish |
| 5,522,801 A | 6/1996 | Wang |
| 5,536,248 A | 7/1996 | Weaver et al. |
| 5,538,511 A | 7/1996 | Van Antwerp |
| 5,599,299 A | 2/1997 | Weaver et al. |
| 5,599,300 A | 2/1997 | Weaver et al. |
| 5,630,823 A | 5/1997 | Schmitz-Rode et al. |
| 5,643,229 A | 7/1997 | Sinaiko |
| 5,653,696 A | 8/1997 | Shiber |
| 5,688,234 A | 11/1997 | Frisbie |
| 5,693,011 A | 12/1997 | Onik |
| 5,715,815 A | 2/1998 | Lorenzen et al. |
| 5,768,741 A | 6/1998 | Leiman et al. |
| 5,772,261 A | 6/1998 | Magram |
| 5,788,678 A | 8/1998 | Van Antwerp |
| 5,788,681 A | 8/1998 | Weaver et al. |
| 5,788,710 A | 8/1998 | Bates et al. |
| 5,807,330 A | 9/1998 | Teitelbaum |
| 5,830,127 A | 11/1998 | DeCastro |
| 5,843,028 A | 12/1998 | Weaver et al. |
| 5,868,720 A | 2/1999 | Van Antwerp |
| 5,895,398 A | 4/1999 | Wensel et al. |
| 5,897,534 A | 4/1999 | Heim et al. |
| 5,902,314 A | 5/1999 | Koch |
| 5,911,710 A | 6/1999 | Barry et al. |
| 5,911,734 A | 6/1999 | Tsugita et al. |
| 5,913,852 A | 6/1999 | Magram |
| 5,921,952 A | 7/1999 | Desmond, III et al. |
| 5,928,218 A | 7/1999 | Gelbfish |
| 5,931,821 A | 8/1999 | Weilbacher et al. |
| 5,957,932 A | 9/1999 | Bates et al. |
| 5,964,223 A | 10/1999 | Baran |
| 5,989,241 A | 11/1999 | Plishka et al. |
| 6,045,623 A | 4/2000 | Cannon |
| 6,080,170 A | 6/2000 | Nash et al. |
| 6,082,361 A | 7/2000 | Morejon |
| 6,129,697 A | 10/2000 | Drasler et al. |
| 6,168,603 B1 | 1/2001 | Leslie et al. |
| 6,183,450 B1 | 2/2001 | Lois |
| 6,248,100 B1 | 6/2001 | de Toledo et al. |
| 6,264,624 B1 | 7/2001 | Desmond, III et al. |
| 6,299,604 B1 | 10/2001 | Ragheb et al. |
| 6,383,196 B1 | 5/2002 | Leslie et al. |
| 6,436,112 B2 | 8/2002 | Wensel et al. |
| 6,454,775 B1 | 9/2002 | Demarais et al. |
| 6,485,497 B2 | 11/2002 | Wensel et al. |
| 6,508,789 B1 | 1/2003 | Sinnott et al. |
| 6,514,273 B1 | 2/2003 | Voss et al. |
| 6,530,935 B2 | 3/2003 | Wensel et al. |
| 6,547,761 B2 | 4/2003 | Liu |
| 6,562,024 B2 | 5/2003 | Alvarez de Toledo et al. |
| 6,582,400 B1 | 6/2003 | Hawk et al. |
| 6,629,956 B1 | 10/2003 | Polidoro et al. |
| 6,638,253 B2 | 10/2003 | Breznock |
| 6,660,014 B2 | 12/2003 | Demarais et al. |
| 6,663,650 B2 | 12/2003 | Sepetka et al. |
| 6,679,262 B1 | 1/2004 | Morejon |
| 6,692,459 B2 | 2/2004 | Teitelbaum |
| 6,692,508 B2 | 2/2004 | Wensel et al. |
| 6,692,509 B2 | 2/2004 | Wensel et al. |
| 6,699,331 B1 | 3/2004 | Kritzler |
| 6,702,830 B1 | 3/2004 | Demarais et al. |
| 6,730,104 B1 | 5/2004 | Sepetka et al. |
| 6,740,096 B2 | 5/2004 | Teague et al. |
| 6,767,338 B2 | 7/2004 | Hawk et al. |
| 6,780,193 B2 | 8/2004 | Leslie et al. |
| 6,783,536 B2 | 8/2004 | Vilsmeier et al. |
| 6,824,545 B2 | 11/2004 | Sepetka et al. |
| 6,849,061 B2 | 2/2005 | Wagner |
| 6,866,657 B2 | 3/2005 | Shchervinsky |
| 6,893,418 B2 | 5/2005 | Liu |
| 6,893,424 B2 | 5/2005 | Shchervinsky |
| 6,905,484 B2 | 6/2005 | Buckman et al. |
| 6,945,977 B2 | 9/2005 | Demarais et al. |
| 7,004,954 B1 | 2/2006 | Voss et al. |
| 7,101,380 B2 | 9/2006 | Khachin et al. |
| 7,125,402 B1 | 10/2006 | Yarger |
| 7,135,010 B2 | 11/2006 | Buckman et al. |
| 7,141,038 B2 | 11/2006 | Whalen et al. |
| 7,211,067 B2 | 5/2007 | Hawk et al. |
| 7,229,433 B2 | 6/2007 | Mullen |
| 7,241,287 B2 | 7/2007 | Shehada et al. |
| 7,241,299 B2 | 7/2007 | Gerard |
| 7,244,251 B2 | 7/2007 | Shehada et al. |
| 7,252,659 B2 | 8/2007 | Shehada et al. |
| 7,264,616 B2 | 9/2007 | Shehada et al. |
| 7,267,671 B2 | 9/2007 | Shehada |
| 7,285,126 B2 | 10/2007 | Sepetka et al. |
| 7,326,197 B2 | 2/2008 | Breznock et al. |
| 7,338,478 B2 | 3/2008 | Leiboff |
| 7,338,501 B2 | 3/2008 | Teague et al. |
| 7,419,483 B2 | 9/2008 | Shehada |
| 7,610,106 B2 | 10/2009 | Yacoubian |
| 7,695,467 B2 | 4/2010 | Breznock et al. |
| 7,780,639 B2 | 8/2010 | Van Lue |
| 7,799,046 B2 | 9/2010 | White et al. |
| 7,811,293 B2 | 10/2010 | Simpson et al. |
| 7,854,728 B2 | 12/2010 | Boyle, Jr. |
| 7,867,241 B2 | 1/2011 | Brock et al. |
| 7,951,243 B2 | 5/2011 | Boyle et al. |
| 7,992,561 B2 | 8/2011 | Baker, Jr. et al. |
| 8,157,919 B2 | 4/2012 | Vazales et al. |
| 2001/0018572 A1 | 8/2001 | Kinsey et al. |
| 2002/0058915 A1 | 5/2002 | Wakabayashi |
| 2002/0128601 A1 | 9/2002 | Reilly |
| 2003/0069551 A1 | 4/2003 | Bradley |
| 2003/0216760 A1 | 11/2003 | Welch |
| 2004/0006331 A1 | 1/2004 | Shchervinsky |
| 2004/0073243 A1 | 4/2004 | Sepetka |
| 2004/0078026 A1 | 4/2004 | Wagner |
| 2004/0089305 A1 | 5/2004 | Vallarta et al. |
| 2004/0092956 A1 | 5/2004 | Liddicoat et al. |
| 2004/0181191 A1 | 9/2004 | Teitelbaum |
| 2004/0219028 A1 | 11/2004 | Demarais et al. |
| 2004/0230132 A1 | 11/2004 | Shehada |

(56) References Cited

U.S. PATENT DOCUMENTS

| | | |
|---|---|---|
| 2005/0033348 A1 | 2/2005 | Sepetka et al. |
| 2005/0055033 A1 | 3/2005 | Leslie et al. |
| 2005/0059995 A1 | 3/2005 | Sepetka et al. |
| 2005/0085849 A1 | 4/2005 | Sepetka et al. |
| 2005/0125024 A1 | 6/2005 | Sepetka et al. |
| 2005/0154373 A1 | 7/2005 | Deutsch |
| 2005/0171478 A1 | 8/2005 | Selmon et al. |
| 2005/0171566 A1 | 8/2005 | Kanamaru |
| 2005/0216030 A1 | 9/2005 | Sepetka et al. |
| 2005/0216050 A1 | 9/2005 | Sepetka et al. |
| 2005/0228363 A1 | 10/2005 | Leiboff |
| 2005/0228417 A1 | 10/2005 | Teitelbaum et al. |
| 2005/0288686 A1 | 12/2005 | Sepetka et al. |
| 2006/0004404 A1 | 1/2006 | Khachin et al. |
| 2006/0142697 A1 | 6/2006 | Hawk et al. |
| 2006/0167416 A1 | 7/2006 | Mathis et al. |
| 2006/0195069 A1 | 8/2006 | Opie et al. |
| 2006/0195137 A1 | 8/2006 | Sepetka et al. |
| 2006/0206097 A1 | 9/2006 | Breznock et al. |
| 2006/0264974 A1 | 11/2006 | Khachin et al. |
| 2006/0264988 A1 | 11/2006 | Boyle |
| 2007/0032779 A1 | 2/2007 | Accisano et al. |
| 2007/0049904 A1 | 3/2007 | Deutsch |
| 2007/0078389 A1 | 4/2007 | Whalen et al. |
| 2007/0083189 A1 | 4/2007 | Lampropoulos et al. |
| 2007/0135795 A1 | 6/2007 | De Paulis |
| 2007/0149946 A1 | 6/2007 | Viswanathan et al. |
| 2007/0179513 A1 | 8/2007 | Deutsch |
| 2007/0198030 A1 | 8/2007 | Martin et al. |
| 2007/0208371 A1 | 9/2007 | French et al. |
| 2007/0288036 A1 | 12/2007 | Seshadri et al. |
| 2008/0045881 A1 | 2/2008 | Teitelbaum et al. |
| 2008/0051720 A1 | 2/2008 | Nash et al. |
| 2008/0091146 A1 | 4/2008 | Solovay et al. |
| 2008/0109032 A1 | 5/2008 | Sepetka et al. |
| 2008/0119869 A1 | 5/2008 | Teague et al. |
| 2008/0177276 A1 | 7/2008 | Teague et al. |
| 2008/0177296 A1 | 7/2008 | Sepetka et al. |
| 2008/0183197 A1 | 7/2008 | Sepetka et al. |
| 2008/0183198 A1 | 7/2008 | Sepetka et al. |
| 2008/0183205 A1 | 7/2008 | Sepetka et al. |
| 2008/0188876 A1 | 8/2008 | Sepetka et al. |
| 2008/0188885 A1 | 8/2008 | Sepetka et al. |
| 2008/0215077 A1 | 9/2008 | Sepetka et al. |
| 2008/0234706 A1 | 9/2008 | Sepetka et al. |
| 2009/0000045 A1 | 1/2009 | Kanno et al. |
| 2009/0048651 A1 | 2/2009 | Andino et al. |
| 2009/0062772 A1 | 3/2009 | Wakeford et al. |
| 2009/0188531 A1 | 7/2009 | Boyle, Jr. et al. |
| 2009/0264833 A1 | 10/2009 | Boyle, Jr. |
| 2009/0326513 A1 | 12/2009 | Deutsch et al. |
| 2011/0023888 A1 | 2/2011 | Vazales et al. |
| 2011/0040285 A1 | 2/2011 | Boyle |
| 2011/0098660 A1 | 4/2011 | Porreca, Jr. |
| 2011/0106019 A1 | 5/2011 | Bagwell et al. |
| 2016/0030984 A1* | 2/2016 | Rife ............ A61B 90/70 134/8 |
| 2020/0038563 A1 | 2/2020 | Boyle, Jr. et al. |

FOREIGN PATENT DOCUMENTS

| | | |
|---|---|---|
| EP | 1197177 A2 | 4/2002 |
| JP | 3930554 B1 | 6/2007 |
| WO | 1989007466 | 8/1989 |
| WO | 1994003226 | 2/1994 |
| WO | 2004098654 A2 | 11/2004 |
| WO | 2004108051 A2 | 12/2004 |
| WO | 2005067647 A2 | 7/2005 |
| WO | 2006071855 A2 | 7/2006 |
| WO | 2006074283 A2 | 7/2006 |
| WO | 2007090057 A2 | 8/2007 |
| WO | 2007098376 A2 | 8/2007 |
| WO | 2008059647 A1 | 5/2008 |

* cited by examiner

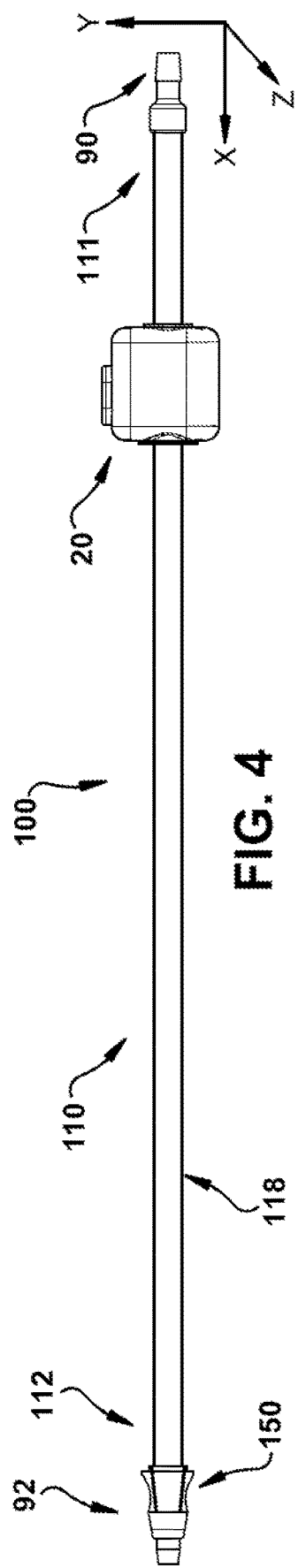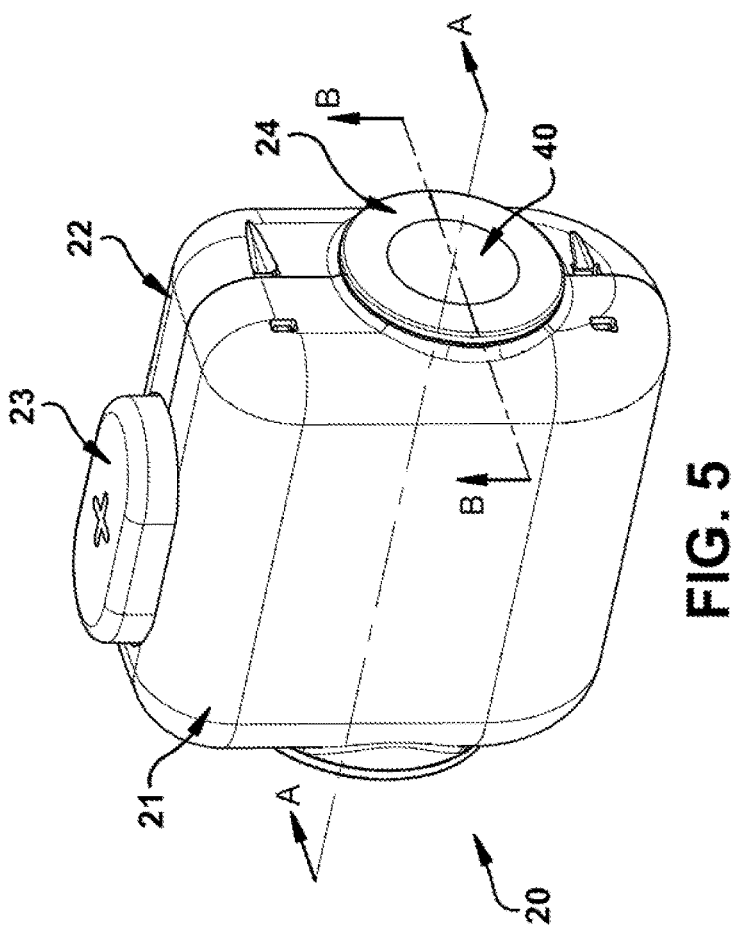
FIG. 4
FIG. 5

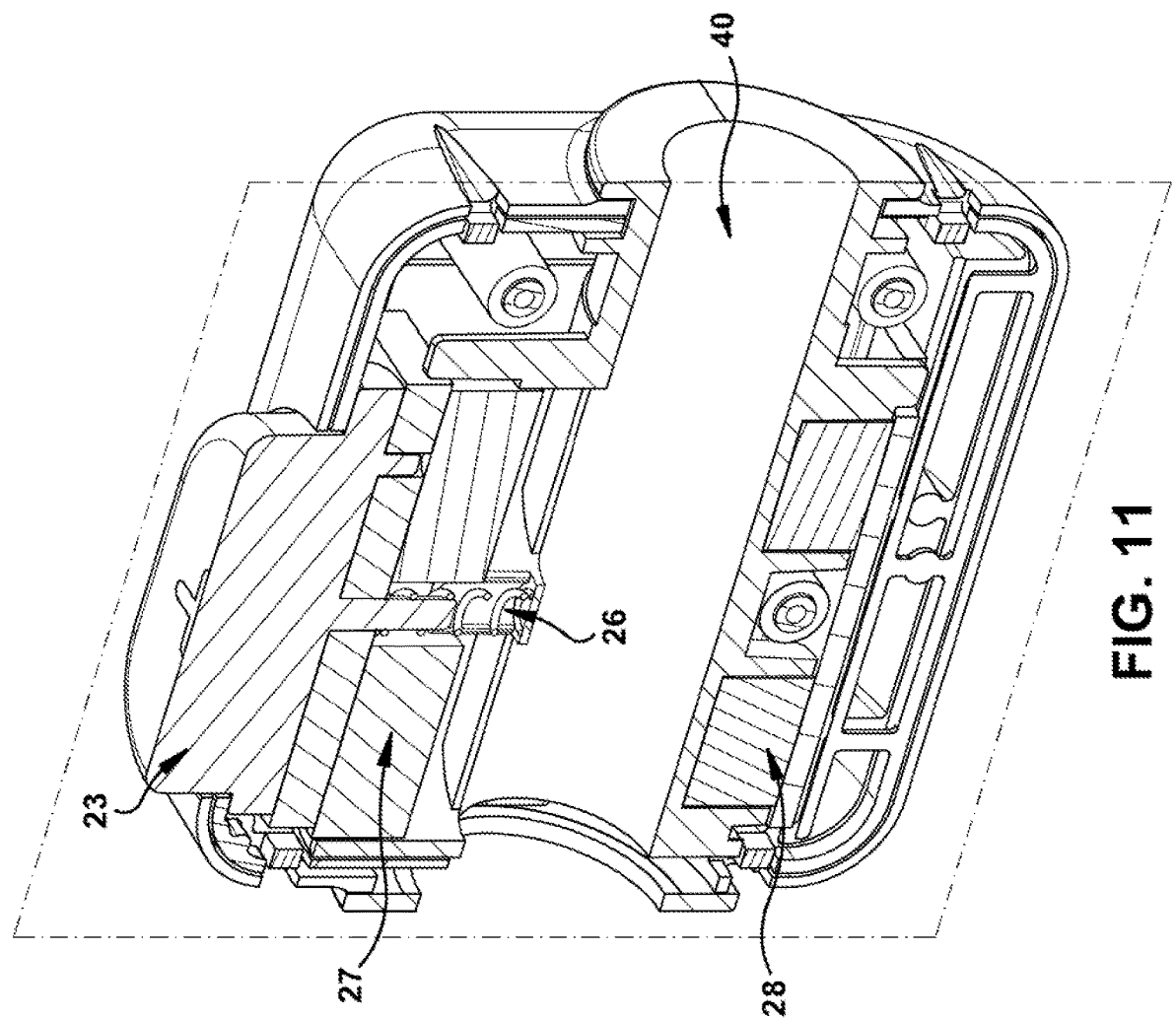

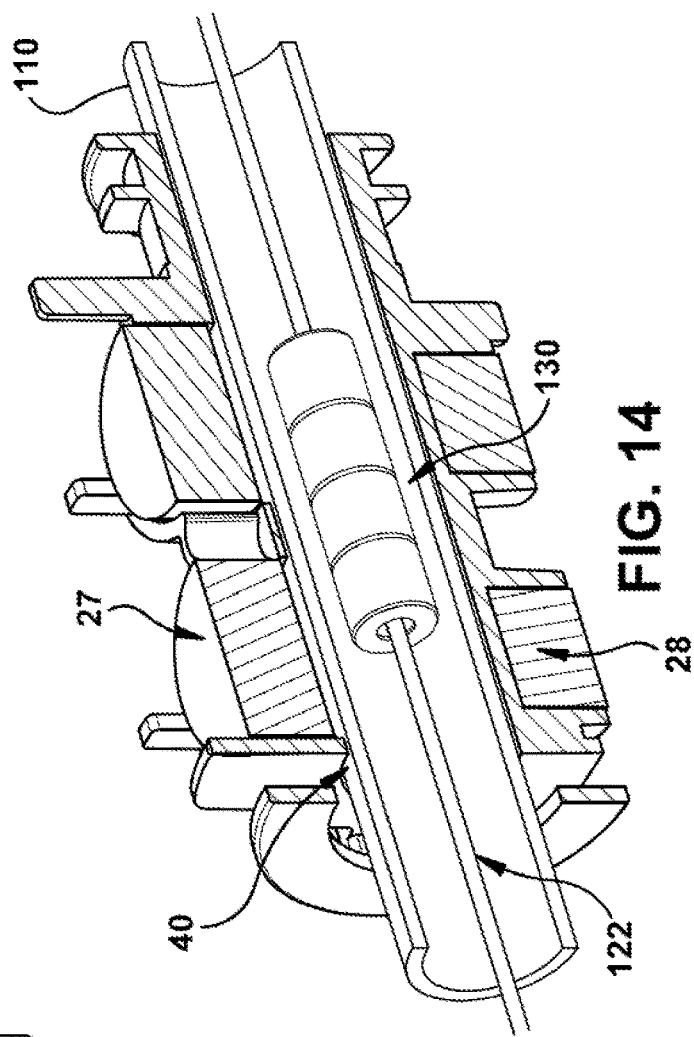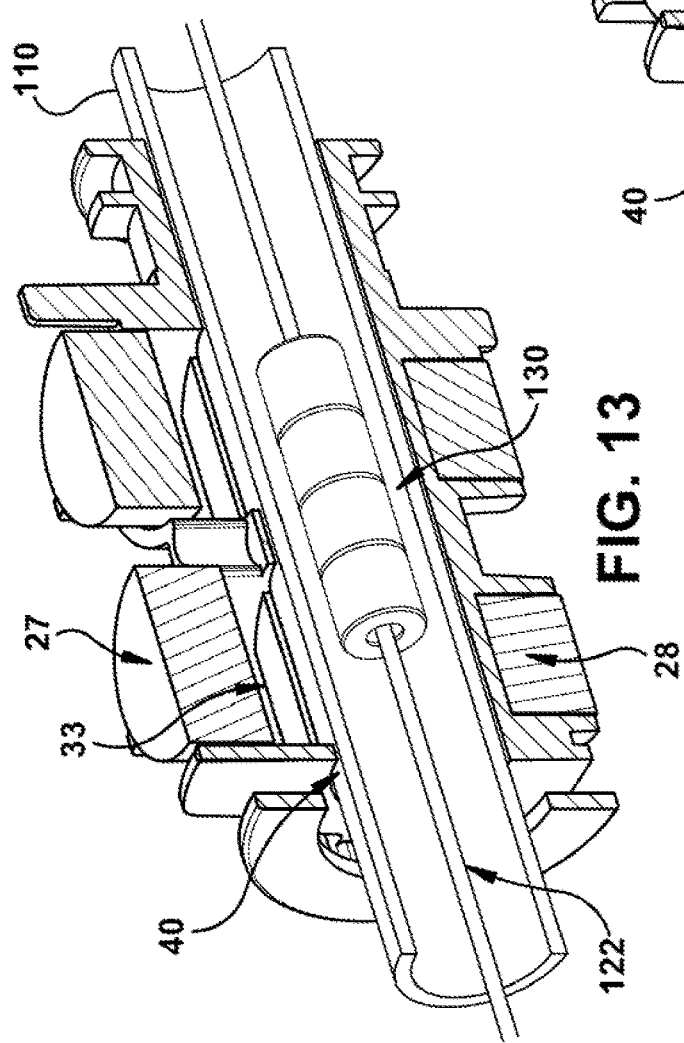

MEDICAL TUBE CLEARANCE DEVICE

TECHNICAL FIELD

This application relates generally to a medical tube assembly and, more specifically, to a device for clearing obstructions from a medical tube of the medical tube assembly.

BACKGROUND

Medical tubes can be used to deliver fluids or devices into a patient's body and/or to drain bodily fluids and secretions from compartments and structures within the body. For example, medical tubes can be used to drain fluid from one's bladder, from the colon or other portions of the alimentary tract, or from the lungs or other organs in conjunction with various therapies. As another example, medical tubes can be used to drain blood and other fluids that typically accumulate within a body cavity following traumatic surgery. As yet another example, medical tubes can be used to deliver fluids to a patient's body for nourishment or they can be used to provide access to the vasculature for removal or delivery of fluids or devices. Typically, a medical tube is inserted into the patient so that its distal end is provided in or adjacent the space where it is desired to remove or deliver material while a proximal portion remains outside the patient's body, where it can be connected, for example, to a suction source.

Fluids passing through a medical tube (particularly those including blood or blood platelets) can form clots or other obstructions within the medical tube, which can partially or totally obstruct the suction pathway within the tube. Obstruction of the medical tube can impact its effectiveness to remove or deliver the fluid and other material for which it was originally placed, eventually rendering the medical tube partially or totally non-functional. In some cases, a non-functional tube can have serious or potentially life-threatening consequences. For example, if there is a blockage in a chest tube following cardiac or pulmonary surgery, the resulting accumulation of fluid around the heart and lungs without adequate drainage can cause serious adverse events such as pericardial tamponade and pneumothorax.

U.S. Pat. No. 7,951,243, incorporated herein by reference, discloses a clearance device for clearing medical tubes (such as chest tubes) of obstructive clot material. That device utilizes a shuttle fitted over a guide tube to actuate a clearance member within the tube via a magnetic coupling between the shuttle and a magnetic guide linked to a guide wire (and corresponding clearance member) within the tube. Based on the arrangement of magnetic elements in the shuttle and the magnetic guide, it is possible for the shuttle to become uncoupled from the magnetic guide during use. For example, this decoupling may occur when there is an obstruction such as a kink or significant clot material in the medical tube such that drag on the guide wire within the tube is stronger than the magnetic-coupling force between the shuttle and the magnetic guide. The embodiments disclosed here address such decoupling and provide improved magnetic coupling between the shuttle and the magnetic guide.

SUMMARY

According to a first aspect, a device for clearing obstructions from a medical tube is disclosed. The device includes a shuttle defining a tube passage configured to accommodate a tube therein and adapted to translate along a length of the tube when accommodated in the passage. The shuttle includes a first primary magnetic element aligned so that a first primary magnetic field axis of a first primary magnetic field thereof is aligned substantially perpendicular to a longitudinal axis of the tube passage when viewed from a side of the shuttle.

According to a second aspect, a device for clearing obstructions includes a shuttle adapted to translate along a length of a tube. The shuttle includes a passage body defining a tube passage having a longitudinal axis configured to accommodate a tube therein. A first primary-magnet recess is disposed in the passage body outside the tube passage. A first primary magnetic element is received in the first primary-magnet recess and has a first primary magnetic field emanating along a first primary field axis that is radially aligned relative to the aforementioned longitudinal axis. A button is operable to slidably adjust the first primary magnetic element within the first primary-magnet recess between a first position radially remote from the tube passage, and a second position radially proximate the tube passage.

According to a third aspect, a method of clearing obstructions from a medical tube is disclosed. The method includes translating a shuttle disposed outside of a tube along a length thereof to correspondingly translate an elongate guide member that is at least partially disposed within the tube and magnetically coupled to the shuttle member through a wall of the tube. A magnetic field emanating from the shuttle is aligned substantially perpendicular to a longitudinal axis of the tube when viewed from a side of the shuttle.

According to a fourth aspect, a device for clearing obstructions includes a shuttle defining a tube passage configured to accommodate a tube therein and adapted to translate along a length of the tube when accommodated in the passage. A first primary magnetic element of the shuttle is adjustable in order to adjust a coupling strength between the first primary magnetic element and a magnetic guide disposed within the tube when received through the tube passage.

BRIEF DESCRIPTION OF THE DRAWINGS

FIG. 3A illustrates a first arrangement of the magnetic elements, and FIG. 3B illustrates a second arrangement of the magnetic elements according to embodiments disclosed herein.

FIG. 4 is a side view of a clearance device having a shuttle according to an example embodiment hereafter described;

FIG. 5 is a perspective view of the shuttle in the clearance device of FIG. 4;

FIG. 11 is a perspective, lateral cross-sectional view of the shuttle taken along the line A-A in FIG. 5;

FIG. 13 is a perspective, lateral cross-section view showing the drive magnets of the shuttle in FIG. 5 in a first position, opposite the secondary magnetic elements relative to a tube passage 40, with other portions of the shuttle removed;

FIG. 14 is a perspective, cross-section view as in FIG. 13 with the drive magnets in a second position;

DETAILED DESCRIPTION

Figure 1:
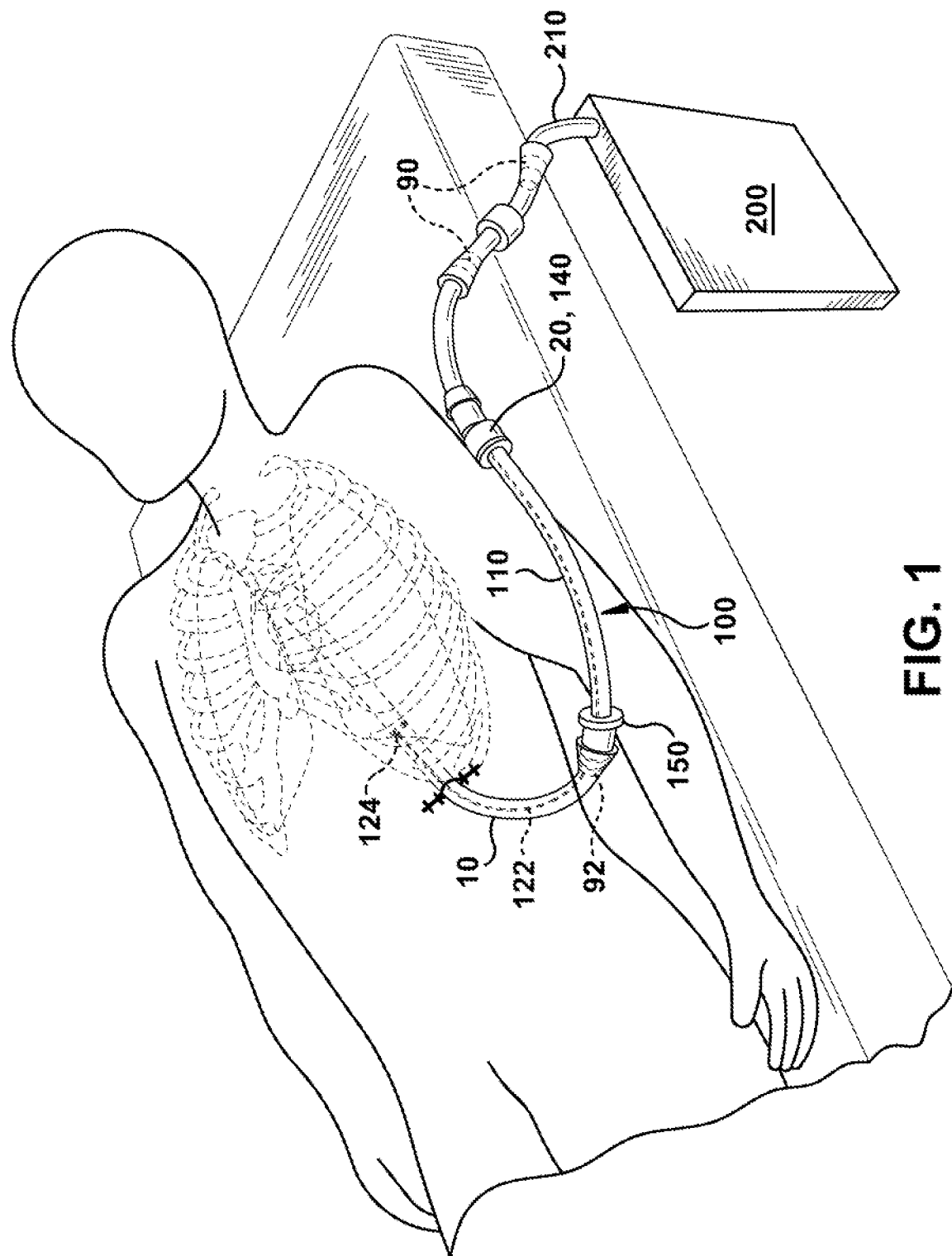
FIG. 1 is a schematic perspective illustration showing a clearance device coupled to a medical tube (e.g., a chest tube) that has been placed in a patient, to permit clearance of the medical tube of obstructions formed therein.

Certain terminology is used herein for convenience only and is not to be taken as a limitation on the present invention. Relative language used herein is best understood with reference to the drawings. Further, in the drawings, certain features may be shown in schematic form.

It is to be noted that the terms "proximal" and "distal" as used herein when describing two ends or portions of a feature indicate a relative positioning that those two ends or portions will generally have along an in-line system relative to a patient, the distal end or portion being closer to (or more advanced within) the patient than the proximal end or portion. For example, in an in-line system comprising a tube that draws fluid from the patient through the tube along a flow path, a distal end or portion of the tube will be closer to (likely implanted within) a patient than a proximal end or portion, which will be outside the patient along the flow path of the fluid.

Examples will now be described more fully hereinafter with reference to the accompanying drawings in which example embodiments are shown. However, aspects may be embodied in many different forms and should not be construed as limited to the embodiments set forth herein.

FIG. 1 shows a schematic representation of a medical tube used to drain accumulated fluid from within a body cavity of a patient, in accordance with an example embodiment. In FIG. 1 the medical tube is inserted into and used to drain fluid from the chest cavity of the patient, and can be, e.g., a chest tube 10 described in the '243 patent incorporated above. The remaining description will be provided with reference to a chest tube 10. However, other body tubes used in other applications could also be used with the embodiments as described herein.

Returning to FIG. 1, the chest tube 10 enters the patient through the chest-cavity (body) wall, so that its distal end is positioned within the chest (body) at a location from which fluid is to be drained. The proximal end of the chest tube 10 remains outside the body. The chest tube 10 can be inserted into the patient in a conventional manner and positioned and secured in place through the chest-cavity wall by a physician. A clearance device 100 is fitted to the proximal end of the chest tube 10. The clearance device 100 can include a shuttle guide tube 110 (described below) that is connected to the proximal end of the chest tube 10 and is provided in fluid communication therewith. The clearance device 100 also includes a clearance member 124 that can be reversibly advanced into and through the chest tube 10 to withdraw obstructive debris therefrom (also described below). The proximal end of the shuttle guide tube 110 (i.e., the end opposite the point of connection to the chest tube 10) is connected to a suction source 200, e.g., via a vacuum tube 210. The suction source draws a suction within the chest tube 10, via the shuttle guide tube 110 (if present) and vacuum tube 210 (if present), both to draw fluid out of the body cavity and to sustain the normal physiologic negative pressure within the chest.

Figure 2:
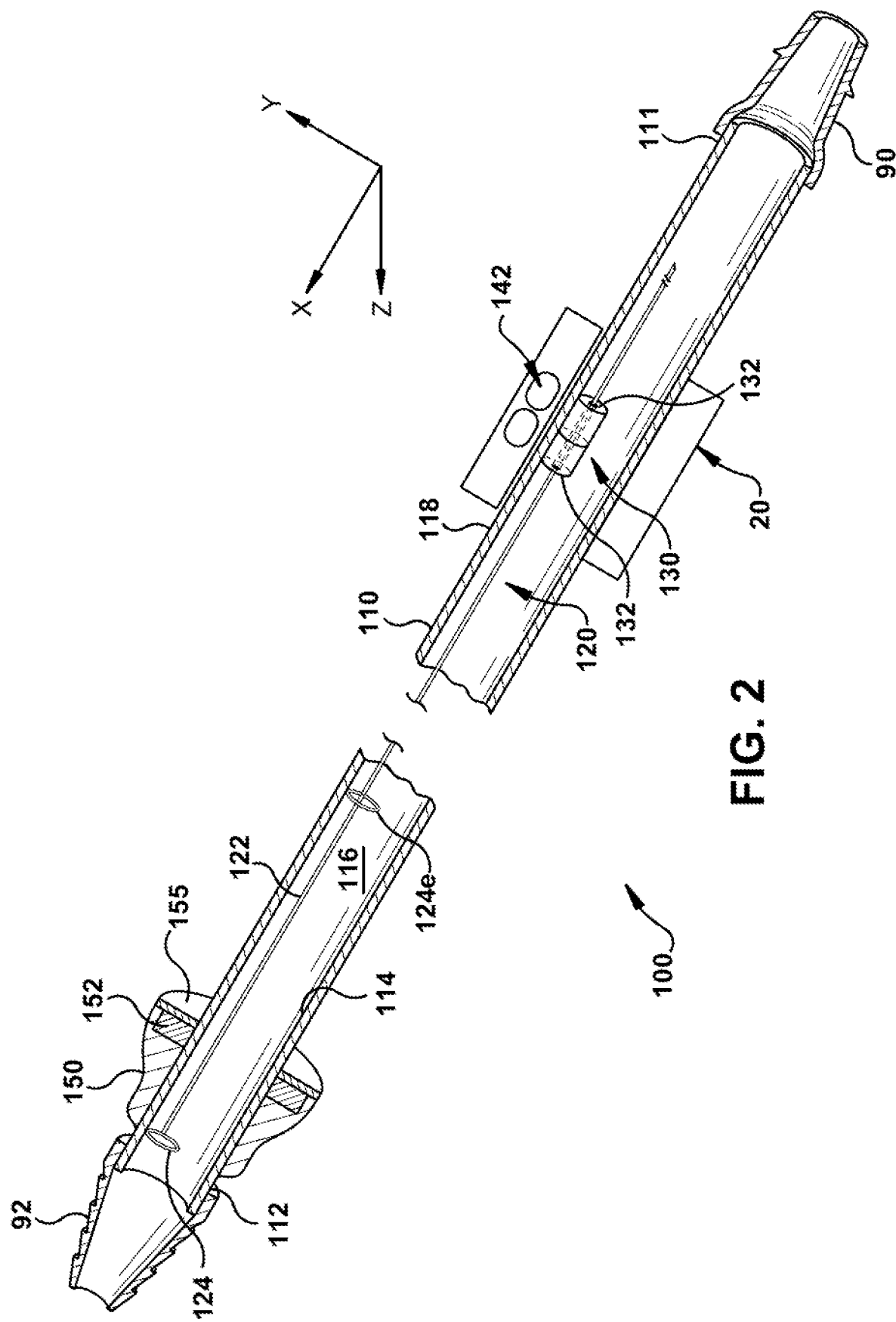
FIG. 2 is a partially sectioned view of a clearance device.

An example clearance device 100 will now be more fully described. As seen in FIG. 2, the clearance device 100 can include the shuttle guide tube 110 mentioned above. The shuttle guide tube 110 has a proximal end 111 and a distal end 112. In use, the proximal end 111 of the shuttle guide tube 110 is adapted to be connected to a suction source, preferably via a suction fitting 90 secured to its proximal end, and the distal end 112 is adapted to be connected to a medical tube, such as the chest tube 10, preferably via a chest-tube fitting 92 secured to its distal end. Guide tube 110 has a wall having an inner diameter 114 defining a guide-tube passageway 116 and an outer circumference 118. A shuttle 20 may be selectively fitted over the guide tube 110 at its outer circumference 118 and is adapted to translate along the length of the tube 110 to advance and withdraw the clearance member 124 as described in detail below. In FIGS. 1, 2 and 15-17 the shuttle 20 is schematically represented. FIGS. 4-14 (described in detail below) illustrate an example embodiment of shuttle 20.

A wire clearance assembly 120 is at least partially disposed within the guide-tube passageway 116. The wire clearance assembly 120 includes an elongate guide member 122 and a clearance member 124 disposed in and secured to the distal region of the guide member 122, preferably at its distal end. In one embodiment, the guide member 122 can be in the form of a guide wire, and the clearance member 124 can be formed by the guide wire, e.g., as a loop. A magnetic guide 130 (e.g., permanent magnets) is secured to the guide member 122 preferably in the proximal region thereof.

As will be evident in FIG. 2, the shuttle 20 magnetically couples to the magnetic guide 130 via outer magnetic elements 142 located within or associated with the shuttle 20. Magnetic elements 142 shown in FIG. 2, can be the primary magnetic elements 27 and secondary magnetic elements 28 (see FIG. 7) as later described. When the North and South poles of the outer magnetic elements 142 are aligned axially, generally parallel to the corresponding (but typically oppositely-oriented) poles of the magnets 132 of the magnetic guide 130, the resulting cooperating magnetic fields between the outer magnetic elements 142 in the shuttle 20 and the magnetic guide 130 are parallel as shown schematically in FIG. 3A.

Figure 3B:
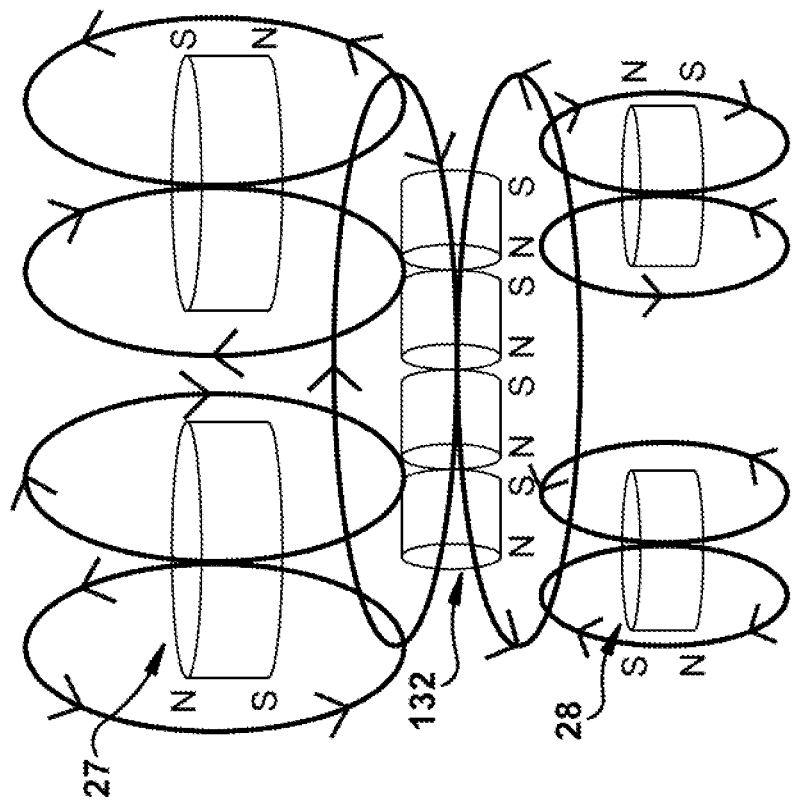
FIGS. 3A and 3B are schematic representations of magnetic fields between magnetic elements in a magnetic guide and magnetic elements in a shuttle of a clearance device for clearing obstructions from a medical tube.
Figure 3A:
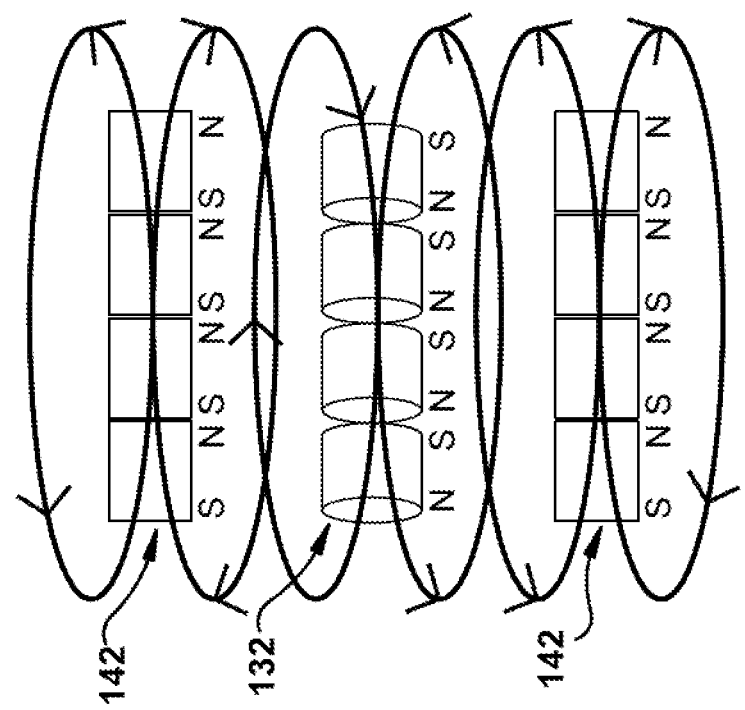
Figure 6:
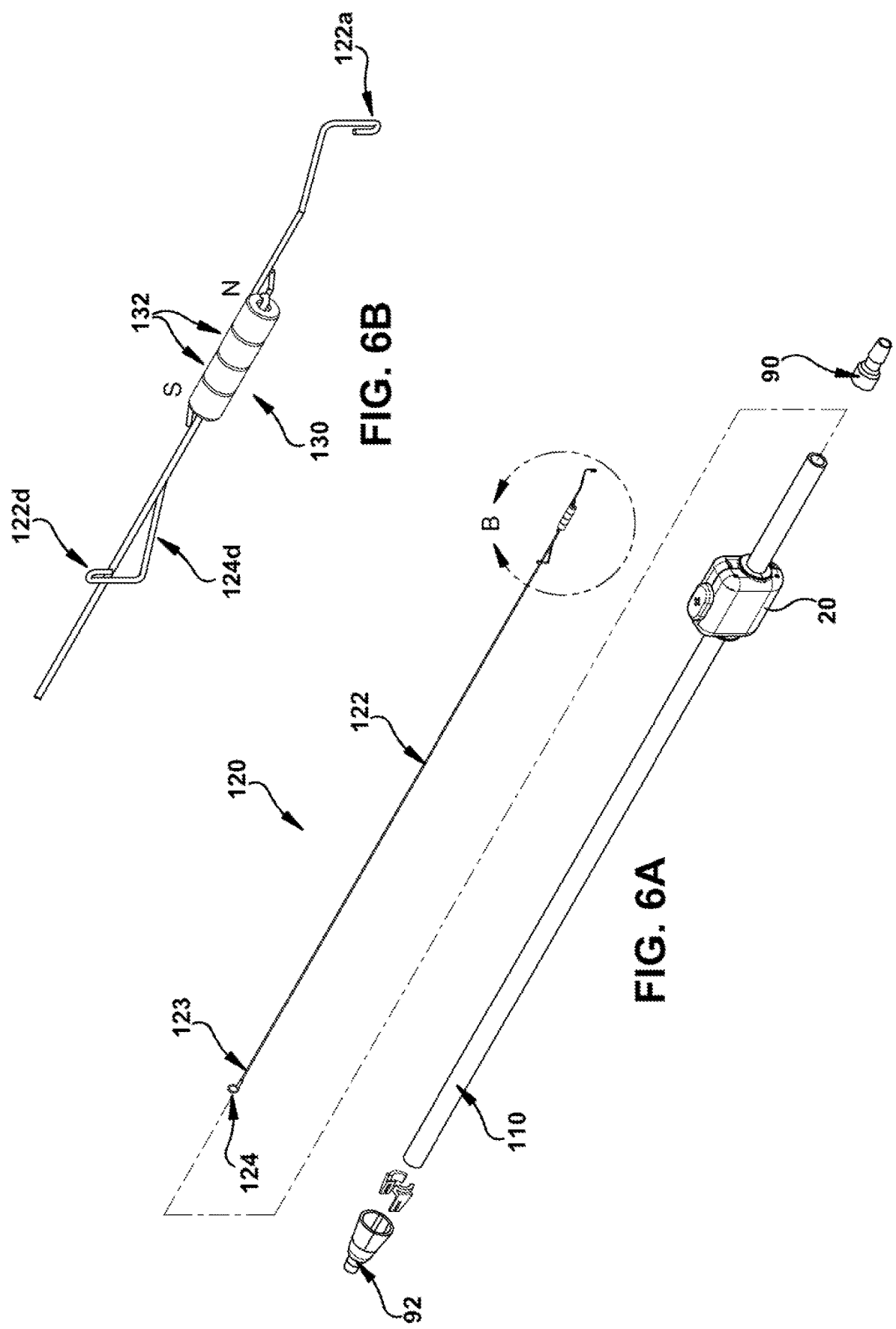
FIG. 6A is a partially exploded view of the clearance device of FIG. 4.
FIG. 6B is a close-up view of a magnetic guide of the clearance device of FIG. 4 shown at B in FIG. 6A.

For magnets of a given magnetic-field strength, such parallel magnetic fields, as shown in FIG. 3A, sometimes may not strong enough to resist decoupling the shuttle 20 from the magnetic guide 130 when the guide member 122 (or the clearance member 124 attached thereto) encounters a robust obstruction within the medical tube 10, which produces drag against which the guide member 122 must translate. When the clearance member 124 encounters such an obstruction, sufficient force must be applied to the clearance member 124 in the X-direction (FIG. 2) to overcome the resistance (drag) provided by the obstruction. When the clearance member 124 engages debris within the chest tube 10, if the amount of force required to move through the debris exceeds the X-direction component of the magnetic coupling force between the magnetic guide 130 and the outer magnetic elements 142 during translation of the shuttle, then decoupling between the shuttle 20 and the magnetic guide 130 occurs.

Such a loss of magnetic coupling between the shuttle 20 and magnetic guide 130 may also occur if a kink in the chest tube 10 produces sufficient drag on the guide member 122 to overcome the X-direction magnetic-coupling force, or for any number of other reasons. While the magnetic coupling may be restored by returning the shuttle 20 to proximity with the magnetic guide 130, one still can face decoupling if the reason they became decoupled persists (as in the case of an obstruction).

FIGS. 4-14 illustrate a clearance device having an example shuttle 20, which yields strong coupling with the magnetic guide 130 through the wall of, e.g., a shuttle guide tube 110. As seen in FIG. 4, the clearance device 100 can include a shuttle guide tube 110 as mentioned above having a proximal end 111 and a distal end 112. In use, the proximal end 111 of the shuttle guide tube 110 is adapted to be connected to a suction source preferably via a suction fitting 90 secured to its proximal end, and the distal end 112 is adapted to be connected to a medical tube, such as a chest tube 10, preferably via a chest-tube fitting 92 secured to its distal end. In an alternative embodiment, not shown, the distal end 112 of the guide tube 110 can be connected to the medical tube via a branched fitting, such as a tee fitting or Y-fitting, wherein guide tube 110 will form a lateral branch off of the main suction circuit defined between the medical tube and a suction source (e.g. via vacuum tube 210) in communication with a third port of the branched fitting. In this manner, the guide wire (discussed below) will be retracted through the guide tube 110 laterally out from the main suction circuit through which secretions are suctioned from the medical tube. Regardless of the particular guide-tube installation (i.e. whether in-line or as a branch off of the main suction circuit, the shuttle 20 is disposed over, preferably in contact with, the wall of the guide tube 110 at its outer circumference 118 (see FIG. 2) and is adapted to translate along the length of the tube 110 in the X-direction to advance and withdraw a wire clearance assembly 120 as described below.

A shuttle stop 150 is secured to the outer circumference 118 of the guide tube 110 in a distal region thereof, preferably just proximal to the distal end of the guide tube 110. The shuttle 20 and shuttle stop 150 can have complementary first and second surfaces that face one another. As the shuttle 20 is translated distally along the length of the guide tube 110, the shuttle 20 approaches and ultimately reaches a position wherein the respective first and second surfaces are in contact or disposed adjacent one another. This represents the distal-most position for the shuttle 20, and therefore the greatest degree of distal advancement of the clearance member 124 within the medical tube 10. Preferably, the position of the shuttle stop 150 is selected, corresponding with the length of the guide member 122, to ensure that the clearance member 124 does not emerge from the distal end of the medical tube 10 in-use.

The wire clearance assembly 120 is configured to be at least partially disposed within the guide-tube passageway 116. As seen in FIG. 6A, the wire clearance assembly 120 includes an elongate guide member 122 and a clearance member 124 disposed in and secured to the distal region of the guide member 122, preferably at its distal end. In one example, the guide member 122 can be in the form of a guide wire, and the clearance member 124 can be formed by the guide wire, which can be wound to form a loop. The remainder of this description is provided with reference to a guide wire as a preferred example of the guide member 122. However, other examples of a guide member 122 are possible and will be readily ascertained by those having ordinary skill in the art.

Still referring to FIG. 6A, a magnetic guide 130 is secured to the guide wire 122, preferably in the proximal region thereof. The magnetic guide 130 can comprise one or a plurality of inner magnetic elements 132. The magnetic elements 132 are considered "inner" magnetic elements because they reside within the guide tube 110. Optionally, the inner magnetic elements 132 can be permanent magnets. Alternatively, they can be metal elements having magnetic properties, which are not necessarily permanent magnets. As used herein, a metal element has magnetic properties if it is capable of being attracted by a permanent magnet via magnetic forces. The magnetic guide 130 can be secured to the guide wire 122 via any suitable or conventional means. FIG. 6B illustrates a close-up view (indicated at "B" in FIG. 6A) of an exemplary magnetic guide 130. In this example, a plurality (four are illustrated) of cylindrically shaped inner magnetic elements 132 having axial through bores are coaxially aligned adjacent to one another. The inner magnetic elements 132 are oriented such that their respective North and South poles face the same direction. This results in the inner magnetic elements 132 attracting one another at their adjacent faces. The guide wire 122, extending from its distal end, passes through the axial bores of the inner magnetic elements 132.

As will also be appreciated, where two or more such inner magnetic elements 132 are used, it is not necessary that both or all are permanent magnets or that both or all are not permanent magnets. The inner magnetic elements 132 may optionally be present as one (or more) of each permanent and non-permanent magnets. However, in examples where retentive forces between them may be relied upon to hold them in place relative to the guide wire 122, using permanent magnets as the inner magnetic elements 132 should produce a stronger attractive force between them, resulting in more securely retaining them to the guide wire 122.

As noted above and most clearly seen in FIG. 4, the shuttle 20 is disposed over, preferably in contact with, the outer circumference 118 of the guide tube 110. The shuttle 20 has a tube passage 40 preferably in the form of a through bore having a diameter substantially corresponding to the outer circumference 118, such that the shuttle 20 can slidably and smoothly translate along the length of the guide tube 110 when that tube is received through its tube passage 40. The shuttle 20 includes a shuttle housing, which in the illustrated embodiment (FIG. 7) is formed of opposing first and second clamshell halves 21 and 22 that form the exterior body of the shuttle 20. A depressible button 23 is accessible through, e.g., stands proud of, the shuttle housing and is used to actuate drive magnets 27 as described below.

Figure 7:
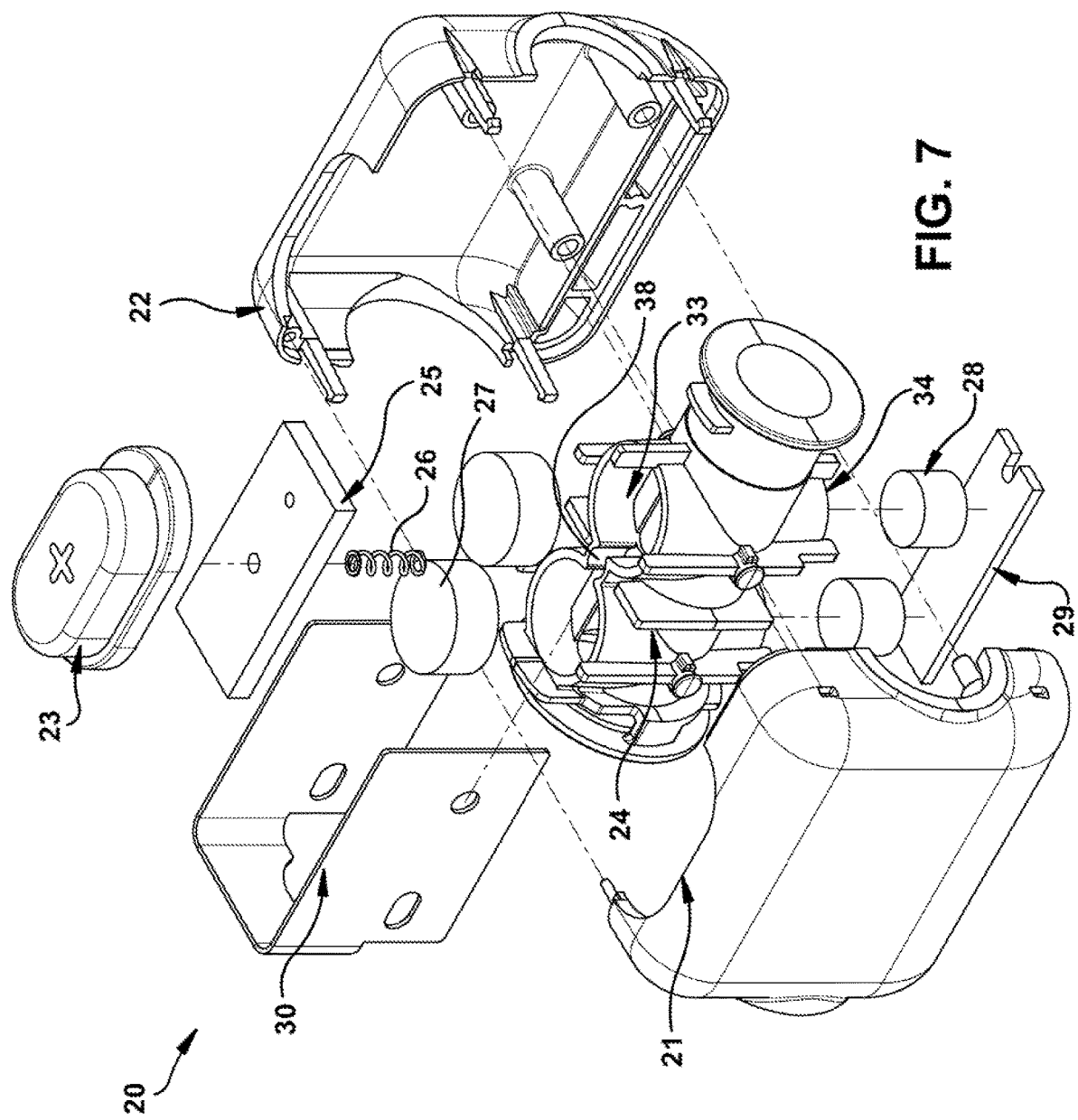
FIG. 7 is an exploded view of the shuttle in FIG. 5.

As illustrated in FIG. 7, the shuttle 20 includes a passage body 24, which defines the aforementioned tube passage 40 to accommodate the guide tube 110 (or the medical tube 10 in embodiments where a guide tube 110 is not used). Alternatively, the tube passage 40 may accommodate a vacuum tube 210; e.g. if no separate guide tube 110 is interposed between the vacuum tube 210 and the medical tube 10. The tube passage 40 in the passage body 24 preferably has an inner surface that is complementary and substantially corresponds to the outer perimeter shape of the guide tube 110, or in the case of a cylindrical tube, its outer circumference 118. One or a plurality of primary-magnet recesses 33 (two are illustrated) are formed in an outer portion of the passage body 24, outside the tube passage 40, and are distributed in longitudinal alignment with the tube passage 40. The recesses 33 preferably are aligned such that respective longitudinal (magnetic-field) axes of magnetic elements to be received therein will be perpendicular to and intersect the longitudinal axis of the tube passage 40. One or a plurality of primary magnetic elements 27 (e.g., drive magnets) are received within the respective recesses 33 of the passage body 24. In the illustrated example, the primary magnetic elements 27 are cylindrical. In other examples, the primary magnetic elements 27 may be any shape that is suitable to fit within the primary-magnet recesses 33 of the passage body 24. Those recesses 33 may be of any desirable shape.

As with the inner magnetic elements 132 discussed above, the primary magnetic elements 27 can be permanent magnets or, alternatively, metal elements having magnetic properties that are not necessarily permanent magnets. However, for reasons that will become clear, either at least one of the inner magnetic elements 132 or at least one of the primary magnetic elements 27 should be a permanent magnet. In preferred examples, both the inner and primary magnetic elements 132 and 27 are permanent magnets. Further, the magnetic guide 130 and the primary magnetic elements 27 may have a residual flux density (Br) of, e.g., 14-15 kGs, such as 14.3 to 14.8 kGs.

FIG. 3B schematically illustrates the arrangement of the inner magnetic elements 132 (e.g., of magnetic guide 130) and the primary magnetic elements 27 when the latter are arranged as in the embodiment of the shuttle illustrated in FIG. 7. (FIG. 3B also illustrates secondary magnetic elements 28, which will be further described below). As seen in FIGS. 3B and 7, the primary magnetic elements 27 (housed in the shuttle 20) preferably are aligned radially relative to the tube passage 40 such that the North and South poles of each are aligned along a radius of the tube passage 40 (and an axis of the particular primary magnetic element 27 when cylindrical) that intersects that passage's longitudinal axis. When two primary magnetic elements 27 are used as drive magnets, they are arranged such that their respective North and South poles face opposite directions. In other words, the North pole of one primary magnetic element 27 faces the tube passage 40 while the South pole of the other primary magnetic element 27 faces the tube passage 40. This results in the two primary magnetic elements 27 creating a single North pole and a single South pole facing the guide tube 110 when received in that passage 40 along a segment thereof defined by the longitudinal spacing of the primary magnetic elements 27. In this manner, and as will be explained further below with respect to FIG. 3B, the resulting magnetic fields from the primary magnetic elements 27 can propagate and be aligned substantially perpendicular to the magnetic field of (and toward) the magnetic guide 130, as opposed to parallel therewith. It is desirable that the spacing between the primary magnetic elements 27 is such that their respective longitudinal (or magnetic-field) axes are substantially aligned with, and preferably intersect, the respective North and South pole ends of the magnetic guide 130 along a longitudinal axis of the magnetic guide 130. Preferably, the South pole of first primary magnetic element 27 faces the North pole of the magnetic guide 130, and the North pole of a second primary magnetic element 27 faces the South pole of the magnetic guide 130.

Figure 9:
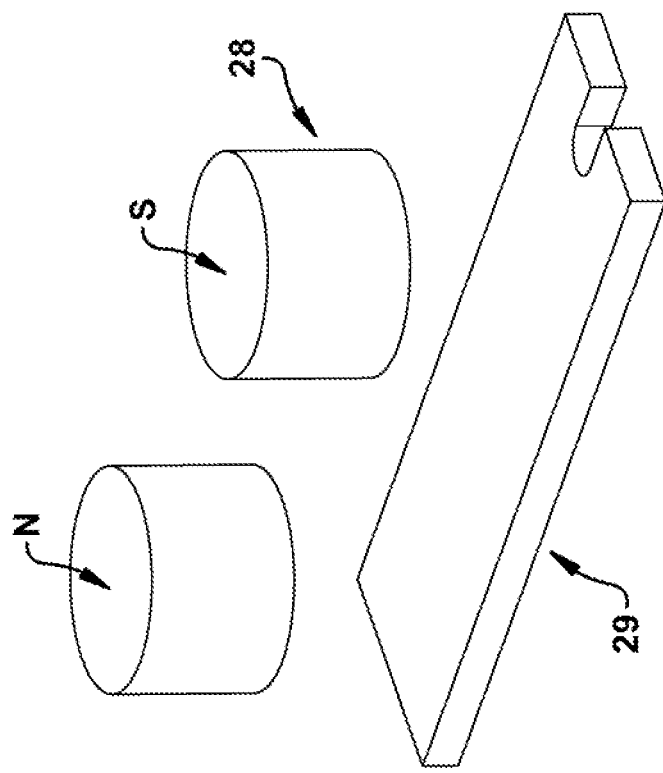
FIG. 9 is a close-up exploded view showing an arrangement of secondary magnetic elements and a secondary shield of the shuttle in FIG. 5, with other elements of the shuttle removed.

As illustrated in FIGS. 7 and 9, the shuttle 20 further includes one or a plurality of secondary magnetic elements 28 radially opposing the primary magnetic elements 27 relative to the tube passage 40 of the passage body 24. Preferably, the secondary magnetic elements 28 are received within corresponding secondary-magnet recesses 34 formed in an outer portion of the passage body 24, outside the tube passage 40, opposing the respective primary-magnet recesses 33 and aligned therewith along common radial axes relative to the passage 40. In the illustrated example, the secondary magnetic elements 28 are cylindrical. In other examples, the secondary magnetic elements 28 may be any shape that is suitable to fit within the secondary-magnet recesses 34 of the passage body 24. The secondary magnetic elements 28 also can be permanent magnets or, alternatively, metal elements having magnetic properties that are not necessarily permanent magnets. However, for reasons that will become clear, either at least one of the inner magnetic elements 132 or at least one of the secondary magnetic elements 28 should be a permanent magnet. In preferred examples, both the inner and secondary magnetic elements 132 and 28 are permanent magnets. Further, the magnetic guide 130 and the secondary magnetic elements 28 may have a residual flux density (Br) of, e.g., 14-15 kGs, such as 14.3 to 14.8 kGs.

In preferred embodiments, the secondary magnetic elements 28 will be longitudinally spaced similarly as (i.e., so that their respective axes align and are co-axial with), but oriented oppositely to, the opposing primary magnetic elements 27. That is, the North/South-pole orientation of each secondary magnetic element 28 should be opposite that of its opposing primary magnetic element 27, so that opposing poles of the respective opposing primary and secondary magnetic elements 27 and 28 face each other opposite the tube passage 40.

As with the primary magnetic elements 27, the secondary magnetic elements 28 are aligned radially relative to the tube passage 40 such that the North and South poles of each secondary magnetic element 28 are aligned along a radius of the tube passage 40 (and an axis of the particular secondary magnetic element 28 when cylindrical) that intersects that passage's longitudinal axis. Thus, similarly as above and explained further below with respect to FIG. 3B, the resulting magnetic fields from the secondary magnetic elements 28 will propagate and be aligned substantially perpendicular to the magnetic field of (and toward) the magnetic guide 130, as opposed to parallel therewith. Preferably, each secondary magnetic element 28 also is aligned along a common radial axis (relative to the tube passage 40) with an opposing primary magnetic element 27 so that their opposing magnetic fields are aligned along their common radial axis and propagate toward one another through the passage body 24.

In the illustrated embodiments, only one set of opposing primary- and secondary magnets 27 and 28 is provided, aligned along a single radius of the tube passage 40 when viewed end-on (i.e. along the longitudinal axis of that passage 40). However, optionally a plurality of sets of opposing primary- and secondary magnets 27 and 28 may be distributed circumferentially relative to the tube passage 40, aligned along respective, circumferentially indexed radii of that passage 40—i.e. such that circumferentially adjacent ones of the respective radii would define an arc sector of the passage 40 when viewed end-on along the longitudinal axis thereof. For example, two sets of opposing primary- and secondary magnets 27 and 28 may be provided, wherein each set is aligned along a respective radius of the tube passage 40 perpendicular to the radius along which the other set is aligned—so that the two radii define four equal-quadrant arc segments of the tube passage 40 when viewed end-on along its longitudinal axis.

Figure 8:
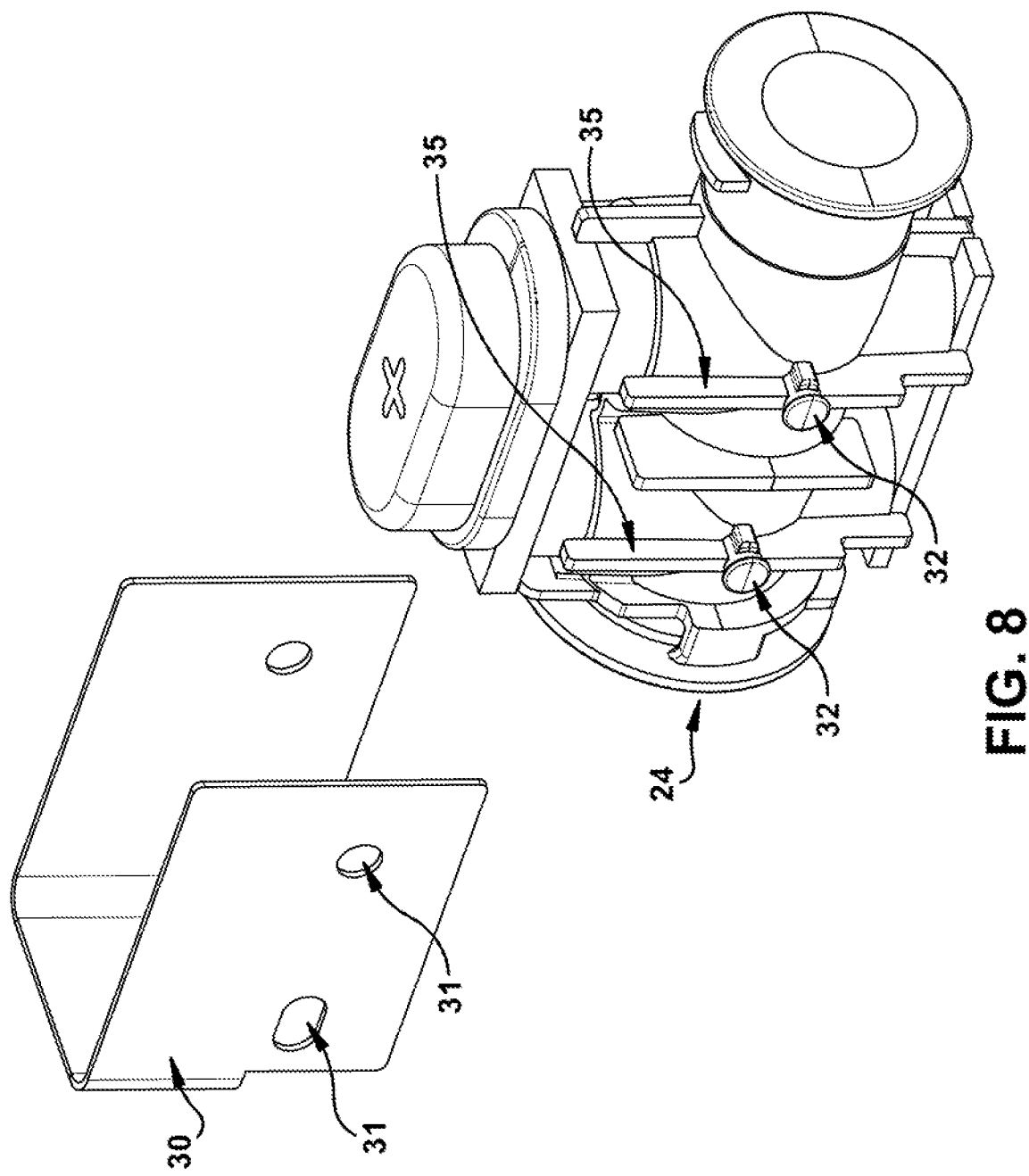
FIG. 8 is a further partially-exploded view of the shuttle in FIG. 5, with the entire housing of the shuttle removed.

The opposing primary- and secondary magnetic elements 27 and 28 provide a strong magnetic coupling to the magnetic guide 130 attached to the guide member 122 within the guide tube 110 (or medical tube 10) to drive the guide member 122 within that tube via translation of the shuttle 20 outside the tube 110, as will be further explained. To reduce interference with surrounding electronic medical equipment or implanted medical devices, the shuttle 20 may incorporate magnetic shielding (e.g., within its housing). For example, a primary magnetic shield 25 can be disposed over exposed surfaces of the primary magnetic elements 27, between them and the button 23 used to adjust them between first and second positions as will be described. Similarly, a secondary magnetic shield 29 can be provided over the exposed surfaces of the secondary magnetic elements 28 (e.g., covering them within the secondary-magnet recesses 34). As illustrated in FIGS. 7 and 8, the shuttle 20 further can include lateral shielding 30 surrounding the primary- and secondary magnetic elements 27 and 28 within the shuttle 20. As shown, the lateral shielding 30 can be a U-shaped element that extends from one side of the passage body 24 to the opposing side of the passage body 24, around an end of the passage body 24. The lateral shielding 30 includes apertures 31 dimensioned to fit over protuberances 32 that extend from opposing sides of the passage body 24 (e.g., from fins 35 formed therein). By aligning the lateral shielding 30 so that the protuberances 32 are secured within apertures 31, appropriate and secure alignment of the shielding 30 can be assured.

The fins 35 extend laterally from the passage body 24 and are dimensioned to appropriately seat the lateral shielding 30 uniformly adjacent to the passage body 24 at a predetermined distance from the primary- and secondary magnetic elements 27, 28. This is useful when the shielding 30 is made of a ferromagnetic material (e.g. low-carbon steel), which in the absence of such fins 35 to correctly seat it and preserve its shape could be drawn and deformed by the magnetic fields of the primary- and secondary magnets 27 and 28. The fins 35 and their associated protuberances also facilitate proper, reproducible alignment and securement of the lateral shielding 30 over the passage body 24 to prevent mis-alignment. Moreover, by fixing the seating position and orientation of the lateral shielding 30, the fins 35 ensure that the shielding 30 remains uniformly spaced from, and does not touch, the magnets 27, 28 or any field-conductive structures communicating with the magnets, which might produce field-shunting. Instead, spaced as described, the lateral shielding 30 will provide far-field magnetic shielding to substantially confine the magnetic fields within the shuttle and minimize escape of those fields.

The primary and secondary magnetic shields 25, 29 and the lateral shielding 30 are preferably made of low-carbon steel. In other examples, they can be made of any material with a high-iron content, e.g. conventional Mu-Metal materials as known in the art. As will be appreciated, the primary magnetic shield 25, secondary magnetic shield 29 and lateral shielding 30 cooperate to magnetically shield the primary- and secondary magnets 27 and 28 within the shuttle 20, inhibiting the propagation of their magnetic fields beyond the shuttle 20. While the combined shielding as described cannot completely enclose the magnetic elements 27 and 28 (because they must magnetically interact with the magnetic guide 130, and accommodate the tube passage 40), it will help to reduce the propagation and strength of the magnetic fields beyond the shuttle 20. It also is noted that when the shuttle 20 is fitted over a tube and aligned with the magnetic guide 130 therein, the combined shielding as described also shields the fields emanating from the magnetic guide 130 (now disposed within the shuttle 20), effectively internally redirecting the combined magnetic fields emanating from the complete magnetic circuit encompassing the interacting primary- and secondary magnetic elements 27 and 28 with the magnetic guide 130. As a result, magnetic-coupling force with the magnetic guide 130 may be increased.

It has been found that adjusting the thickness of the primary and secondary magnetic shields 25, 29 (e.g. made of low-carbon steel) can impact the magnetic-coupling strength with the magnetic guide 130. For example, increased thickness of the primary magnetic shield 25 will result in greater shunting of the respective magnetic fields from one primary magnetic element 27 to the other; effectively helping to drive the combined primary magnetic fields radially inward toward the tube passage 40 axis (and the magnetic guide 130). This will tend to strengthen the coupling force between the primary magnetic elements 27 and the magnetic guide 130 within a tube received through the tube passage 40. Similarly, increased thickness of the secondary magnetic shield 29 will yield greater shunting of the respective magnetic fields between the secondary magnetic elements 28. This will reinforce the magnetic coupling between the secondary magnetic elements 28 and the magnetic guide 130. It may be useful to tune the respective primary and secondary magnetic shield 25,29 thicknesses in order to optimize coupling with the magnetic guide 130. That is, increased coupling force between the primary magnetic elements 27 and the magnetic guide 130 may yield stronger available translational (axial) force to the guide member 122 (and clearance member 124) attached to the magnetic guide 130, via translation of the shuttle 20. However, such increased coupling force also will increase transverse (radial) forces between the magnetic guide 130 and the inner diameter of the tube wall, leading to increased friction. Increasing coupling force between the secondary magnetic elements 28 and the magnetic guide 130 may lessen that effect by drawing the magnetic guide 130 away from the tube wall adjacent to the primary magnetic elements 27. By tuning the relative thicknesses between the primary and secondary magnetic shields 25, 29, these competing effects (available translational force through coupling, versus friction) may be optimized. For low-carbon steel, shield thickness preferably is within the range of 0.01 to 0.25 inches, more preferably 0.025 to 0.175 inches for both the primary and secondary magnetic shields 25 and 29. Meanwhile, increasing the thickness of the lateral shielding independently can help reduce escaping of the magnetic fields emanating from within the shuttle to the extraneous environment.

FIG. 3B schematically illustrates the primary- and secondary magnetic elements 27 and 28 oriented and aligned as disclosed, relative to (example inner magnetic elements 132 of) the magnetic guide 130, and their resultant, cooperating magnetic fields. As seen in the figure, the magnetic fields of the primary- and secondary magnetic elements 27 and 28 propagate along axes aligned perpendicular with the axis of the magnetic field emanating from the magnetic guide 130 (e.g., from elements 132 thereof). It has been found that with the magnetic fields aligned in this fashion, the magnetic attraction between the shuttle 20 (via its primary/secondary magnetic elements 27, 28) and the magnetic guide 130 can be quite strong, resulting in improved coupling between the shuttle 20 and the magnetic guide 130 during use. Accordingly, more force may be applied to the clearance member 124 in the X-direction without decoupling the shuttle 20 from the magnetic guide, in order to overcome drag resistance introduced by an obstruction encountered by the clearance member 124 within the chest tube 10.

For example, a conventional shuttle 20 having high field-strength rare-earth, neodymium magnets configured as rings as described in the '243 patent, coupled to similar-composition neodymium magnets in the magnetic guide 130, typically delivers approximately 0.4 lbf of translational force to the clearance member 124 in the X-direction before the shuttle 20 becomes decoupled from the magnetic guide 130. This is the amount of force available to overcome drag introduced by an obstruction in the medical tube 10. Whereas using the primary- and secondary magnetic elements 27 and 28 aligned to orient their opposing magnetic fields radially toward the magnetic guide 130 against a similarly constituted magnetic guide 130 as disclosed here, the shuttle 20 herein has been shown to deliver up to approximately 1.2 lbf of translational force to the clearance member 124 before decoupling from the magnetic guide 130; i.e., about three times the available translation force compared to the prior-art device. The increased available translational force is a result of stronger magnetic attraction between the magnetic elements in the shuttle 20 and those in the magnetic guide 130 during use, believed to be a result of orienting the primary- and secondary magnetic elements 27 and 28 as herein disclosed. The result is greater ability to overcome and clear robust obstructions in the medical tube 10, and reduced incidence of shuttle-decoupling.

Further, it is believed that both the primary- and secondary magnetic shields 25 and 29 help to strengthen the effective magnetic attraction between the primary and secondary magnetic elements 27 and 28, respectively, and the magnetic guide 130. Specifically, the primary magnetic shield 25 couples the opposing poles of adjacent primary magnetic elements 27, which reinforces their magnetic fields by completing a circuit between the primary magnetic elements 27. The secondary magnetic shield 29 acts in a similar manner to reinforce the magnetic fields of the secondary magnetic elements 28 by completing a circuit therebetween. This results in a greater ability to overcome and clear obstructions in the medical tube 10, and reduced incidence of shuttle-decoupling.

As will be appreciated, the maximum available magnitude of the strong magnetic coupling between the shuttle 20 and the magnetic guide 130 through the tube wall will not be necessary at all times to translate the clearance member 124. For example, in the absence of obstructions or in the presence of minor obstructions, minimal coupling force may be required to translate the clearance member 124. In such instances, maximum coupling force between the shuttle 20 and the magnetic guide 130 may be undesirable, because it will increase the frictional force against sliding the shuttle 20 along the tube 110, thus making the device 100 more cumbersome to use routinely. It also will increase the frictional force between the internal magnetic guide 130 and the ID of the tube 110. Accordingly, the shuttle 20 includes a mechanism to operate at reduced magnetic coupling strength, and to increase the magnitude of the coupling strength to a maximum degree only when desired by the operator to clear or traverse a robust obstruction in the medical tube 10.

Figure 10:
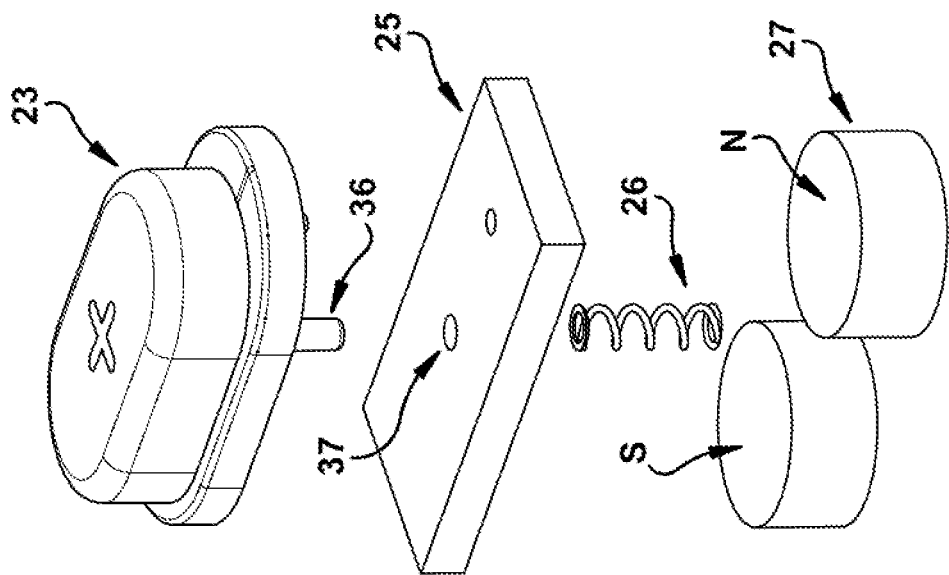
FIG. 10 is a close-up exploded view showing an arrangement of drive magnets, a drive shield, a spring, and a button of the shuttle in FIG. 5, again with other elements of the shuttle removed.

Specifically, as illustrated in FIGS. 7 and 10 and noted above, the shuttle 20 includes the depressible button 23, e.g., arranged on a face of the primary magnetic shield 25 opposite the primary magnetic elements 27. In one example, the button 23 includes a boss 36 that extends from its underside through a central aperture 37 in the primary magnetic shield 25, and through a spring 26 positioned between the primary magnetic elements 27. Opposite the primary magnetic shield 25, the spring 26 is seated and rests against the passage body 24, e.g., within a radial passage or spring recess 38 defined between the primary-magnet recesses 33. In this manner, the spring 26 biases the primary magnetic shield 25 and the button 23 at its opposite face in a position radially remote from the passage body 24. Preferably, the primary magnetic elements 27 are adhered (e.g. via magnetic interaction) to the underside surface of the magnetic shield, so that the primary magnetic elements 27 are similarly biased radially away from the tube passage 40, corresponding to a first position of the primary magnetic elements 27 (FIG. 13) as hereafter described. Whereas, depressing the button 23 radially inward drives the primary magnetic shield 25 and the attached primary magnetic elements 27 radially inward, against the spring bias, preferably until they become seated against respective floors of the primary-magnet recesses 33 in a second position of those elements 27 (FIG. 14), also hereafter described.

As illustrated in, e.g., FIGS. 11 and 13, the secondary magnetic elements 28 are fixed within the secondary-magnet recesses 34 of the passage body 24. Conversely, the primary magnetic elements 27 can be adjusted through a range of radial positions relative to the tube passage 40 of the passage body 24, e.g., between the aforementioned first and second positions. Because the radial positions of the secondary magnetic elements 28 are fixed, the field strength available from the secondary magnetic elements 28 for translating the magnetic guide 130 (and thereby the clearance member 124) is not manually adjustable. However, one can manually adjust the field strength available from the primary magnetic elements 27 to drive the magnetic guide 130 by operating the button 23, thereby adjusting the primary magnetic elements 27 between the first and second positions as will be further explained.

Referring to FIG. 13, the primary magnetic elements 27 are shown in the first (resting) position. With the magnetic guide 130 disposed within the tube passage 40 of the shuttle 20 (inside of the tube 110 received therethrough), the primary and secondary magnetic elements 27, 28 are magnetically attracted to the magnetic guide 130 from opposing radial directions. And as the shuttle 20 translates along the guide tube 110, the magnetic attraction between the magnetic elements 27, 28 of the shuttle 20 and the magnetic guide 130 induces movement of the clearance member 124 within the chest tube 10, e.g., to remove obstructions within the chest tube 10. This translational movement with the primary magnetic elements 27 in their first (resting) position, remote from the tube passage 40, generally is sufficient for routine clearing of the chest tube 10 at predetermined intervals.

However, if the clearance member 124 encounters a robust obstruction within the chest tube 10, additional force in the X-direction may be required to traverse or dislodge the obstruction and continue translating the clearance member 124 along its course through the chest tube 10. In such instances, the button 23 may be pressed to thereby advance the primary magnetic elements 27 radially inward, toward or into their second position, seated within the respective primary-magnet recesses 33 adjacent to the tube passage 40.

In such radially advanced (e.g., their second) position, the primary magnetic elements 27 become more recessed within the recesses 33, closer to the magnetic guide 130 within the tube 110 received in the tube passage 40 of the shuttle 20, as illustrated in FIG. 14. When the primary magnetic elements 27 are located closer to the magnetic guide 130, the magnetic attraction force between the primary magnetic elements 27 and the magnetic guide 130 is increased, which enables the shuttle 20 to apply stronger translational force to the clearance member 124 in the X-direction before it will decouple from the magnetic guide 130.

While the primary magnetic elements 27 are shown in the first and second positions in FIGS. 13 and 14, it will be appreciated that those positions represent the boundaries of the adjustable range. The primary magnetic elements 27 may be adjusted to any point between those positions to yield corresponding adjustment to the strength of the magnetic coupling between primary magnetic elements 27 and the magnetic guide 130. For example, if a slight increase of available force in the X-direction is desired, the button 23 can be only slightly depressed, e.g., to reduce the radial distance between the primary magnetic elements 27 and the magnetic guide 130 by 10%, 15%, 20%, 25%, or some other fraction less than 100%. If additional force in the X-direction is desired, the button 23 may be depressed further, e.g., to reduce that radial distance even further such as by 30%, 35%, 40%, 45%, 50%, or more. A user may depress the button 23 and decrease the distance between the primary magnetic elements 27 and the magnetic guide 130 by any amount between the first and second positions of the primary magnetic elements 27. The spring 26 biases the button 23 (and primary magnetic elements 27) to the fully radially withdrawn (i.e., 'resting') position, and thus will oppose any depression of the button 23. In this manner, a user may adjust the degree of field-strength increase by modulating the degree to which the button 23 is pressed against the spring bias. And once the operation is completed, the spring 26 returns the button 23 (and primary magnetic elements 27) to the fully radially withdrawn, 'resting' position.

In one example, the radial (relative to the tube passage 40) distance between the primary and secondary magnetic elements 27, 28 (with the primary magnetic elements 27 fully radially engaged and seated against their floors of the respective primary-magnet recesses) is 0.5 inches, 0.75 inches, 0.85 inches, 0.95 inches, or 1 inch; e.g., depending on the diameter of the tube passage 40 adapted to accommodate a particular tube 110 therein. By positioning the magnetic guide 130 between the primary and secondary magnetic elements 27, 28, theoretically the magnetic guide 130 could be magnetically, radially suspended in a generally central position within the tube 110 inside the tube passage 40. Although this theoretical possibility typically will not be realized in practice, the fact that the magnetic guide 130 is nonetheless drawn in opposing directions between the primary- and secondary magnetic elements 27, 28 can reduce frictional forces between the magnetic guide 130 and the guide tube passageway as the shuttle 20 is operated to translate the clearance member 124. As a result, the amount of force available for X-direction translation of the clearance member 124 may be increased upon translation of the shuttle 20 along the tube 110.

Figure 12:
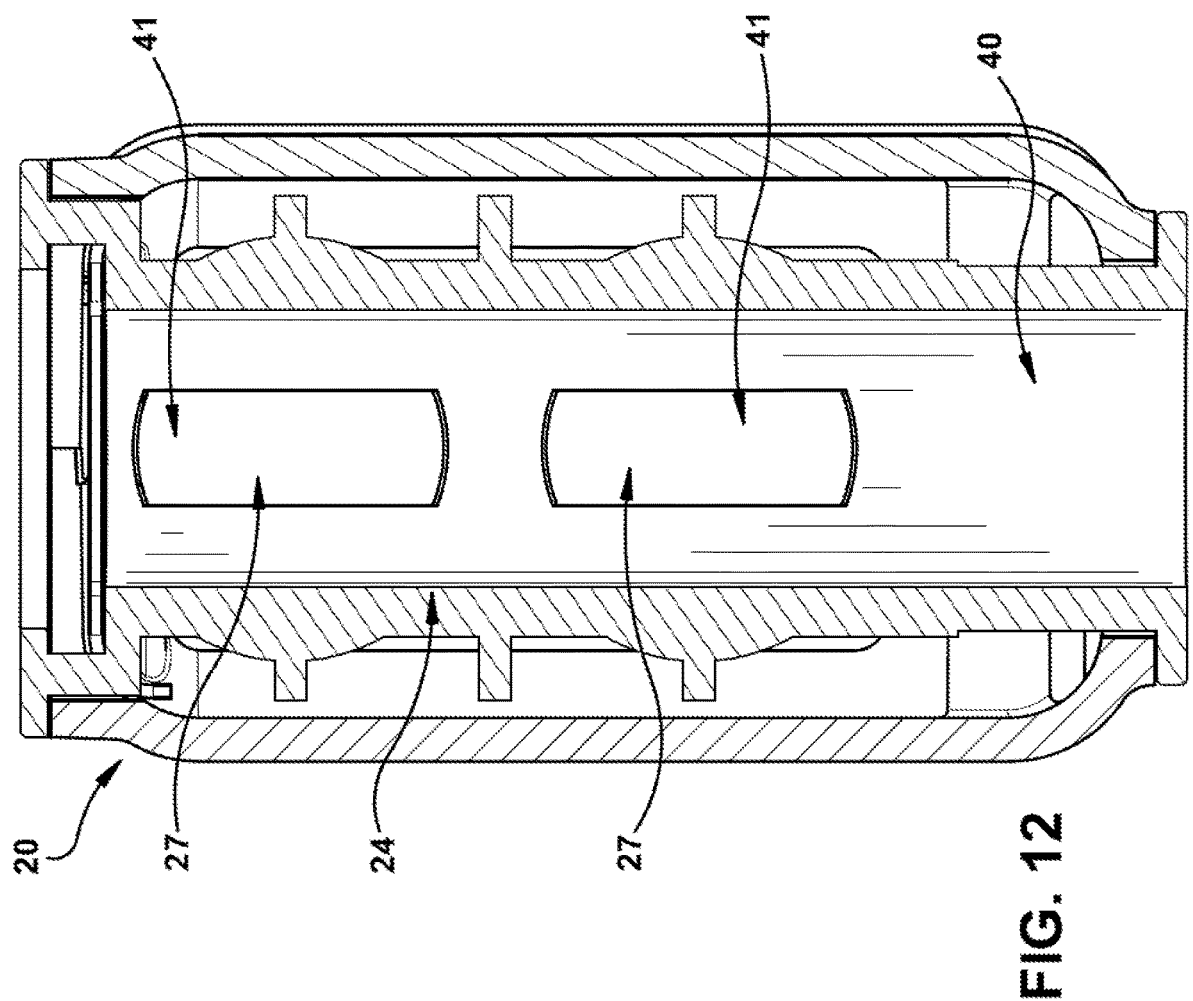
FIG. 12 is a cross-sectional view of the shuttle taken along the line B-B in FIG. 5.

In order to maximize the field strength (if that is desired) between either (or both) the primary- and the secondary magnetic elements 27, 28 and the magnetic guide 130 within a tube 110 received in the tube passage 40, the radial distance therebetween should be as small as possible. In one example, the radial distance between, e.g., the primary magnetic elements 27 and the magnetic guide 130 can be reduced by introducing apertures 41 in the base wall of each primary-magnet recess 33, thereby effectively reducing the outer diameter of the tube passage 40 in the vicinity of the respective recess 33 so that the primary magnetic elements 27 may be driven radially more inward. This is shown in FIG. 12. By removing a portion of the passage body 24 constituting the circumferential wall of the tube passage 40 in the vicinity of the recesses 33, the primary magnetic elements 27 can be seated more radially inward, nearer to the inner diameter of (or even partially within) the tube passage 40. Also optionally, if desired similar apertures can be provided in the floor of each secondary-magnet recess 34 to permit a greater degree of radially-inward fixation of the secondary magnetic elements 28. However, in practice such apertures in the floors of the secondary-magnetic recesses 34 are less preferred because some degree of spacing is desirable to diminish their coupling force (and thereby the resulting frictional force against translation of either the shuttle 20 or the magnetic guide 130) when stronger coupling to overcome an obstruction in the tube (via depressing button 23) is not required.

In the embodiments described, the coupling strength of the magnetic fields between the primary magnetic elements 27 in the shuttle 20 and the magnetic guide 130 within a tube received in the tube passage 40 can be adjusted by adjusting the radial position of the primary magnetic elements 27. The foregoing embodiments also disclose two primary magnetic elements 27 and two secondary magnetic elements 28. However, an alterative embodiments the shuttle 20 may possess only one primary magnetic element 27 opposing one secondary magnetic element 28 along a common radius relative to the tube passage 40 as already described. In addition, the primary magnetic element(s) 27 need not be adjustable. Rather, the primary magnetic element(s) can be in a fixed position.

Figure 15:
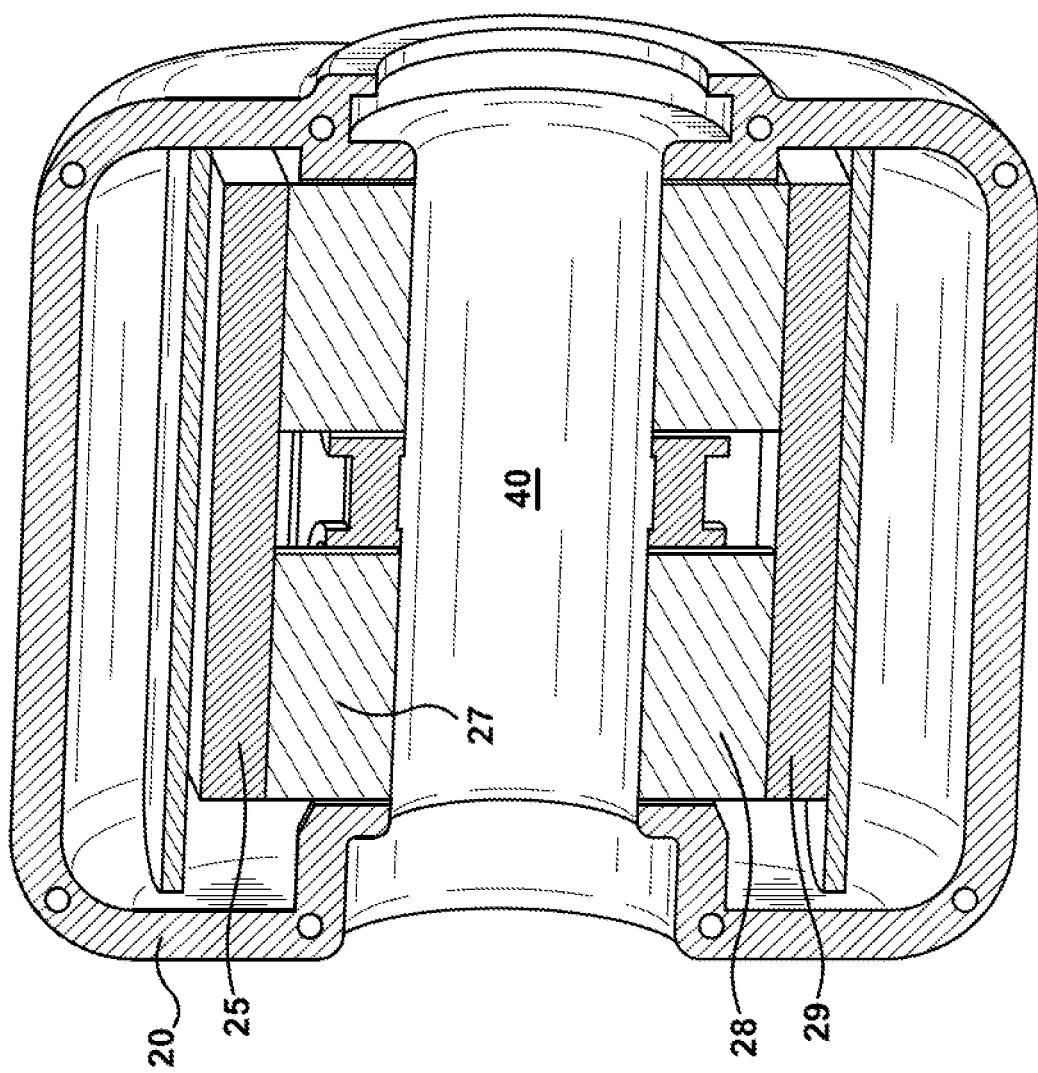
FIG. 15 is a perspective, cross-sectional view of shuttle according to an alternative embodiment.

FIG. 15 illustrates a partial cross-sectional view of a shuttle 20 as already described, but wherein the primary magnetic elements 27 are not adjustable. In this embodiment, the coupling strength between the primary magnetic element 27 and the magnetic guide 130 will not be adjustable. This embodiment is desirable from an ease-of-manufacture standpoint, though it will not possess adjustable coupling strength with the magnetic guide 130 as in other disclosed embodiments.

Figure 16:
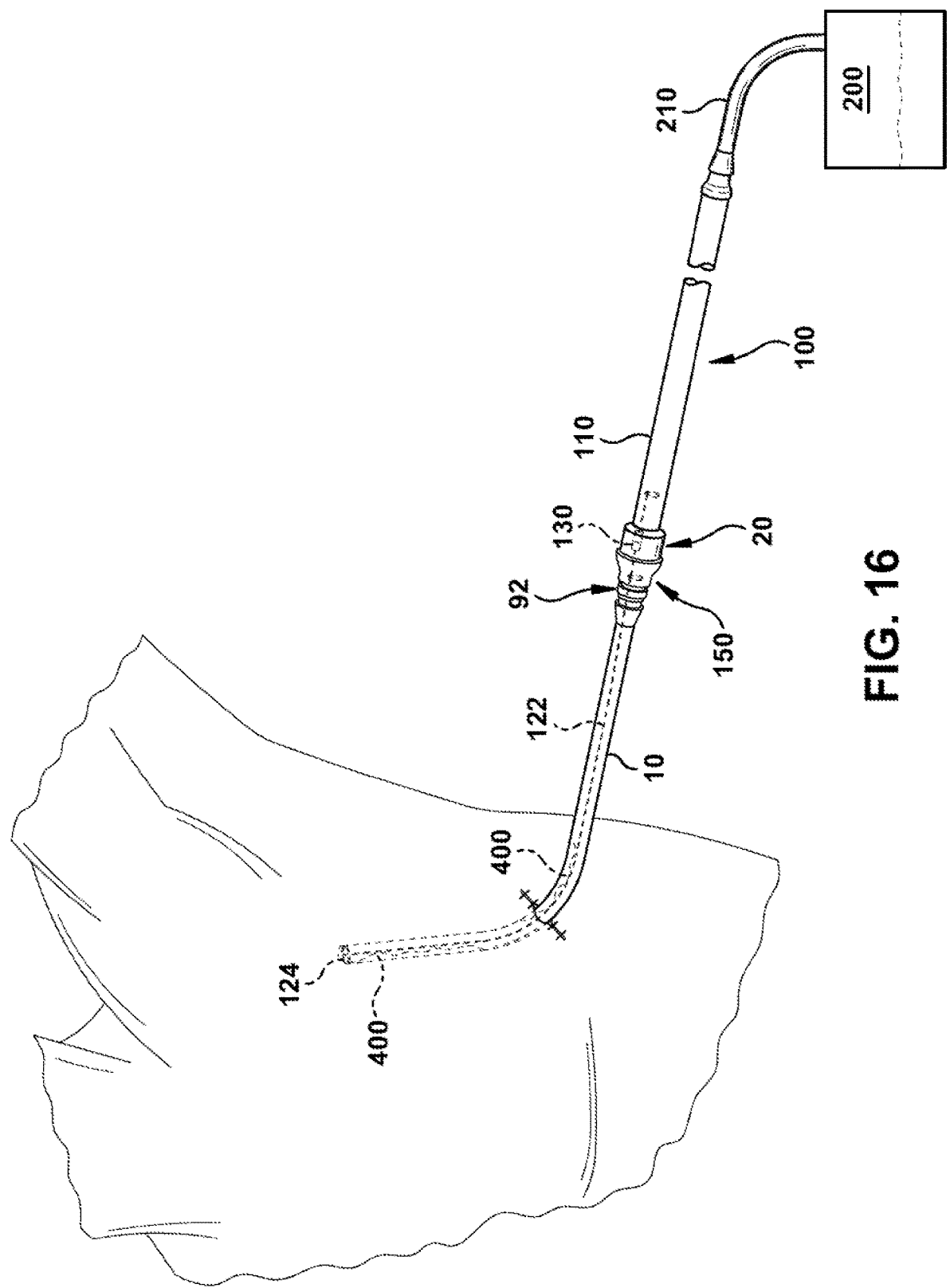
FIGS. 16-18 are perspective views of a clearance device coupled to a chest tube schematically showing the shuttle, and correspondingly the guide wire and clearance member, at different stages of advancement for clearing obstructions from the chest tube, ranging from fully advanced in FIG. 16 to fully withdrawn in FIG. 18.
Figure 17:
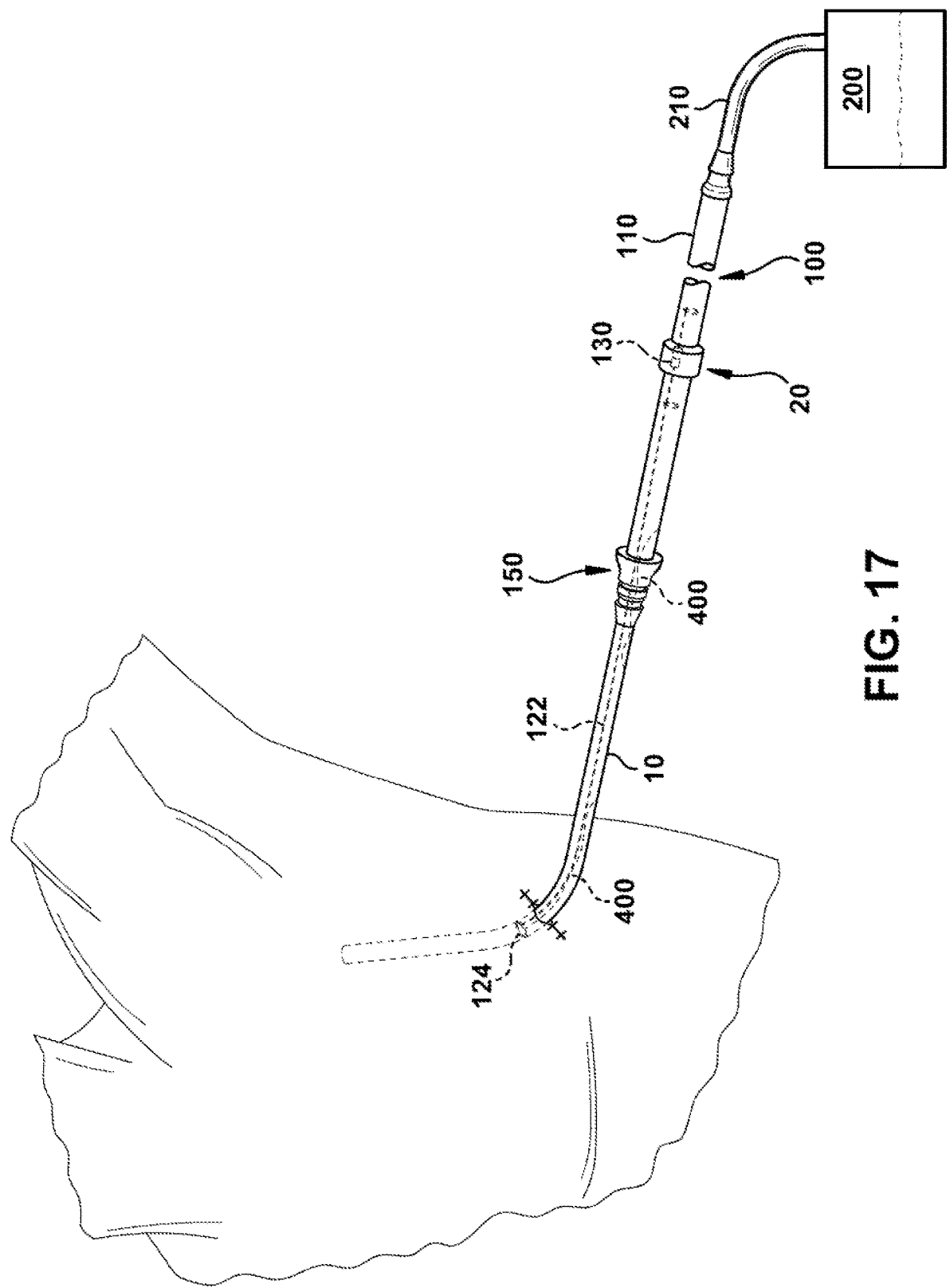
Figure 18:
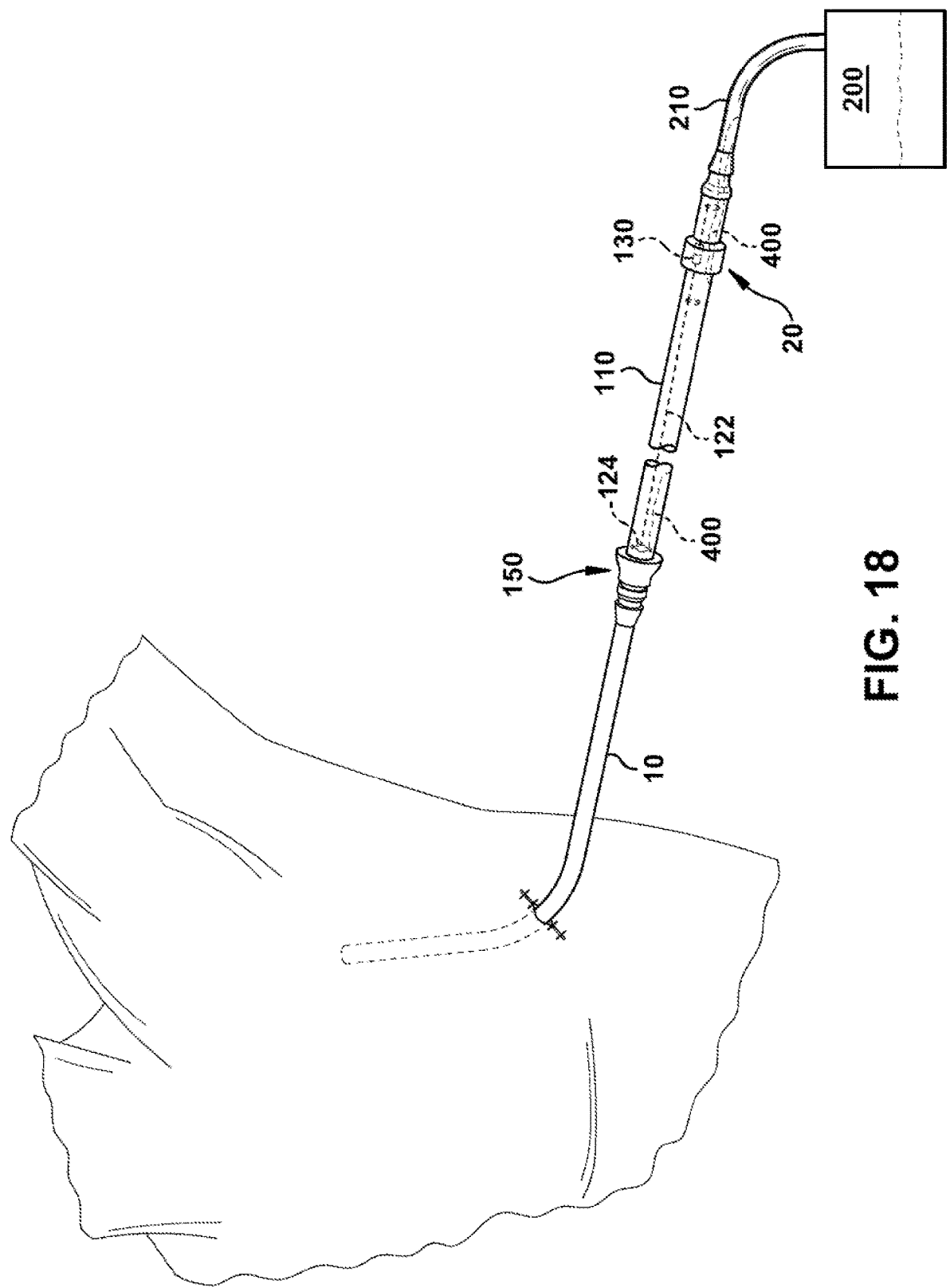

Referring now to FIGS. 16-18, a clearance device 100 as described herein is shown fitted to a chest tube 10 via a chest-tube fitting 92 that ensures a fluid-tight connection between the distal end of the shuttle guide tube 110 and the proximal end of the chest tube 10, while providing fluid communication between the chest-tube passageway and the guide-tube passageway 116. The chest tube 10 has a wall having an outer circumference and an inner diameter that defines a chest-tube passageway.

With the clearance device 100 and chest tube 10 fitted together as described above, the guide member 122, and the clearance member 124 disposed at its distal end, may be advanced into and withdrawn from the chest tube 10 to assist in clearing debris therefrom as follows. In use, the magnetic guide 130 and the primary- and secondary magnetic elements 27, 28 of the shuttle 20 are magnetically attracted and coupled to one another when the shuttle 20 is fitted or properly positioned over the guide tube 110. This results in coupling the magnetic guide 130 to the shuttle 20 via magnetic forces that act through the guide tube 110 wall. Consequently, longitudinally sliding or translating the shuttle 20 along the length of the shuttle guide tube 110 induces a corresponding translational movement of the magnetic guide 130 magnetically coupled thereto, and of the guide member 122 that is secured to the magnetic guide 130. In FIG. 16, the shuttle 20 (shown schematically) is illustrated in a first position, in contact with the shuttle stop 150. The length of the guide member 122 between its distal end and the point where it is secured to the magnetic guide 130 is preferably selected to substantially equal the length of the chest tube 10 plus the length corresponding to the distance between the shuttle stop 150 and the point where the chest tube 10 engages the fitting 92. In this embodiment, when the shuttle 20 is positioned against the shuttle stop 150 (having the magnetic guide 130 in tandem therewith along the guide-tube 110 length), the clearance member 124 at the distal end of the guide member 122 is disposed within the chest tube 10 adjacent to its distal end and does not emerge from the chest tube 10 into the body cavity. In a preferred embodiment, this is the first position of the clearance member 124, where it normally rests when the clearance device 100 is not being used to actively remove debris from the chest tube 10.

In operation, with the chest tube 10 (its distal end) inserted in a body cavity of a patient and the shuttle guide tube 110 being connected to a suction source 200 at its proximal end, fluid from the body cavity is drawn into and through the chest-tube passageway, then through the guide-tube passageway 116 to be collected or disposed of in any suitable or conventional manner, such as in a conventional collection canister (not shown). (Alternatively, as noted above the guide tube 110 may be branched from the main suction circuit defined between a medical tube 10 and a vacuum tube 210, in which case fluid from the body cavity will be drawn primarily through that main suction circuit and not through the guide tube 110). In the illustrated embodiment, the clearance member 124 is in the form of a wire loop that scrapes the inner diameter of the chest tube 10 as it translates along the chest-tube 10 length.

As noted above, the clearance member 124 (e.g., a loop) is normally disposed adjacent the distal end of the chest tube 10 inside the chest-tube passageway. To help clear the chest tube 10 of clots and other debris 400 accumulated therein, the shuttle 20 is disposed over the tube 110, so that it is magnetically coupled with the magnetic guide 130 within the tube 110. When so fitted, and once it is magnetically coupled with the magnetic guide 130 within the tube 110, a nurse, physician, or other operator then pulls the shuttle 20 proximally along the length of the guide tube 110, toward the tube's 110 proximal end. The attractive magnetic force between the magnetic guide 130 and the primary- and secondary magnetic elements 27, 28 of the shuttle retains the magnetic guide 130 in tandem with the shuttle 20 as the latter translates proximally. This in turn draws the guide member 122 and clearance member 124 proximally through the chest-tube passageway as seen in FIG. 17. As the clearance member 124 is drawn proximally, it engages clot material and other debris 400 in its path and forces such material and debris proximally (FIGS. 17, 18), toward the proximal end of the chest-tube passageway and ultimately out of that passageway, into the guide-tube passageway 116 (FIG. 18). To carry out this operation, preferably the operator grasps the shuttle 20 with one hand and the proximal end of the guide tube 110 with the other hand so that the pulling force applied to the shuttle 20 is applied against a counterforce applied to the tube 110 via the other hand, and not against the sutures retaining the chest tube 10 in place in the patient. Alternatively, the same objective can be achieved by grasping a different portion of the guide tube 110, or the shuttle stop 150, with the other hand before sliding the shuttle 20. Optionally, the clearance member 124 can be alternately withdrawn and advanced from/into the chest-tube passageway to help break up clot material or other debris, as well as to aid in drawing such debris proximally. Once the clearance operation has ended, the shuttle 20 may be used to restore the magnetic guide 130, and consequently the clearance member 124, to its resting position.

In case additional translational force is desired to traverse or dislodge a robust clot within the chest tube 10, the user can depress the button 23 on the shuttle 20 to radially advance the primary magnetic elements 27 toward the tube passage 40 therein, thereby strengthening the field between the shuttle 20 and the magnetic guide 130.

In the embodiments where such a button 23 is provided, it has been described as actuating both the primary magnetic elements 27 shown in the figures simultaneously. However, in select embodiments one primary magnetic element 27 can be normally (or full-time) fully radially advanced (or seated) toward or against the tube passage 40 of the passage body 24, wherein actuation of the button 23 advances (or withdraws) a second (or more) primary magnetic element(s) 27 to adjust the coupling field strength. Or a plurality of buttons 23 as described can be provided, one for each primary magnetic element 27 so that those magnetic elements 27 can be individually and selectively radially advanced in order to adjust the coupling strength with the magnetic guide 130 within a tube received through the tube passage 40. In addition, while the button 23 has been described as a depressible button 23, it be replaced with a rocker switch or another kind of switch to radially advance the primary magnetic element(s) 27. Optionally, for example, the button 23 (or other switch) can include a locking feature to lock it in the fully radially advanced position (or in a different, e.g. user-selected degree of advancement) if desired.

As will be appreciated, while the shuttle 20 is being used to actuate a clearance member 124 within a medical tube 10, if it becomes de-coupled from the magnetic guide 130 within the guide tube 110, the shuttle 20 and the magnetic guide 130 may be magnetically re-coupled by advancing the shuttle 20 forward (or backward) until magnetic coupling is re-established. Alternatively, the operator may squeeze the chest tube 10 or guide tube 110 to manually engage the guide member 122 through the tube wall and hold it in position while the shuttle 20 is translated so as to magnetically re-engage the magnetic guide 130 through the guide-tube 110 wall. In addition to facilitating translation of the guide member 122 via magnetic coupling between the (magnetic elements of the) shuttle 20 and the magnetic guide 130, the disclosed embodiments also facilitate rotation of the guide member 122 within the chest tube 10/guide tube 110 by rotating the shuttle 20 about the exterior of that tube. The transversely aligned magnetic fields from the respective and opposing first and second magnetic elements 27, 28 within the shuttle 20 are magnetically coupled to the magnetic guide 130 in a fixed orientation. Therefore, rotating the shuttle 20 about the tube correspondingly rotates the magnetic guide 130 (and the guide member 122 to which it is attached) within the tube as a result of that fixed orientation. This may be useful to help clear obstructive debris within the tube, as well as for navigating obstructions or tortuosity resulting from curves or bends in the tube (for example due to kinks therein).

Although the invention has been described with respect to certain preferred embodiments, it is to be understood that the invention is not limited by the embodiments herein disclosed, which are exemplary and not limiting in nature, but is to include all modifications and adaptations thereto as would occur to the person having ordinary skill in the art upon reviewing the present disclosure, and as fall within the spirit and the scope of the invention as set forth in the appended claims.

What is claimed is:

1. A device for clearing obstructions, comprising:
a shuttle defining a tube passage configured to accommodate a tube therein and adapted to translate along a length of said tube when accommodated in said tube passage, the shuttle comprising a first primary magnetic element aligned so that a first primary field axis of a first primary magnetic field thereof is aligned substantially perpendicular to a longitudinal axis of said tube passage when viewed from a side of said shuttle, said first primary magnetic element being adjustable between a first position remote from the tube passage and a second position proximate the tube passage.

2. The device of claim 1, said shuttle further comprising a second primary magnetic element aligned so that a second primary field axis of a second primary magnetic field thereof is aligned substantially perpendicular to the longitudinal axis of said tube passage when viewed from the side of said shuttle.

3. The device of claim 2, a North pole of said first primary magnetic element facing said tube passage, and a South pole of said second primary magnetic element facing said tube passage.

4. The device of claim 3, further comprising a tube received in said tube passage and having a magnetic guide therein, wherein said first primary field axis is substantially aligned with a South-pole terminus of said magnetic guide along said longitudinal axis, and said second primary field axis is substantially aligned with a North-pole terminus of said magnetic guide along said longitudinal axis.

5. The device of claim 1, said shuttle further comprising a first secondary magnetic element aligned so that a first secondary field axis of a first secondary magnetic field thereof is aligned substantially perpendicular to the longitudinal axis of the tube passage when viewed from the side of said shuttle.

6. The device of claim 5, said first primary magnetic element and said first secondary magnetic element opposing one another relative to said tube passage such that the first primary field axis and the first secondary field axis are radially aligned relative to said longitudinal axis of said tube passage.

7. The device of claim 6, further comprising a tube received in said tube passage and having a magnetic guide therein, wherein said first primary field axis and said first secondary field axis are substantially aligned with a South-pole terminus of said magnetic guide along said longitudinal axis.

8. The device of claim 5, said shuttle further comprising a second secondary magnetic element aligned so that a second secondary field axis of a second secondary magnetic field thereof is aligned substantially perpendicular to the longitudinal axis of said tube passage when viewed from the side of said shuttle.

9. The device of claim 5, wherein the first secondary magnetic element is fixed within the shuttle.

10. The device of claim 5, further comprising a secondary magnetic shield arranged adjacent to an exposed surface of the first secondary magnetic element.

11. The device of claim 1, further comprising a tube received in said tube passage and having a magnetic guide therein, wherein a strength of magnetic coupling between the magnetic guide and first primary magnetic element is adjustable by adjusting the first primary magnetic element between said first and second positions.

12. The device of claim 1, said shuttle further comprising a button that is spring biased radially away from said tube passage, wherein depressing said button against the spring bias urges said first primary magnetic element from the first position toward the second position.

13. The device of claim 1, further comprising a primary magnetic shield arranged adjacent to an exposed surface of the first primary magnetic element.

14. The device of claim 13, the shuttle further comprising a lateral magnetic shield that extends from one lateral side of the tube passage to an opposing lateral side of the passage.

15. The device of claim 14, the shuttle further comprising a passage body that defines said tube passage, said lateral magnetic shield comprising ferromagnetic material and being seated on a fin that extends laterally from said passage body, said fin being dimensioned to preserve a shape of said lateral shielding against deformation induced by said first primary magnetic field.

16. The device of claim 15, the fin comprising a protuberance configured to fit within an aperture of said lateral magnetic shield.

17. The device according to claim 1, the shuttle further comprising a passage body that defines said tube passage and comprises a primary recess configured to receive the first primary magnetic element.

18. A device for clearing obstructions, comprising a shuttle adapted to translate along a length of a tube, said shuttle comprising:
a passage body defining a tube passage having a longitudinal axis configured to accommodate a tube therein, and a first primary-magnet recess disposed outside the tube passage;
a first primary magnetic element received in the first primary-magnet recess and having a first primary magnetic field emanating along a first primary field axis that is radially aligned relative to said longitudinal axis; and
a button operable to slidably adjust the first primary magnetic element within the first primary-magnet recess between a first position radially remote from said tube passage and a second position radially proximate said tube passage.

19. The device of claim 18, said shuttle further comprising a first secondary magnetic element having a first secondary magnetic field emanating along a first secondary field axis radially aligned with and opposing said first primary field axis relative to said longitudinal axis.

20. The device of claim 19, said shuttle further comprising a primary magnetic shield arranged adjacent to an exposed surface of the first primary magnetic element, a lateral magnetic shield extending from one lateral side of the passage body to an opposing lateral side of the passage body, and a secondary magnetic shield arranged adjacent to an exposed surface of the first secondary magnetic element, said lateral magnetic shield comprising ferromagnetic material and being seated on a fin that extends laterally from said passage body, said fin being dimensioned to preserve a shape of said lateral shielding against deformation induced by said first primary magnetic field.

21. The device of claim 19, said passage body further defining a second primary-magnet recess disposed outside the tube passage adjacent to and spaced from the first primary-magnet recess along said longitudinal axis; said shuttle further comprising:

a second primary magnetic element received in the second primary-magnet recess and having a second primary magnetic field emanating along a second primary field axis that is parallel to said first primary field axis and radially aligned relative to said longitudinal axis; and a second secondary magnetic element adjacent to and spaced from the first secondary magnetic element along said longitudinal axis, said second secondary magnetic element having a second secondary magnetic field emanating along a second secondary field axis radially aligned with and opposing said second primary field axis relative to said longitudinal axis;

said button being operable to commonly adjust both said first and said second primary magnetic elements within the respective first and second primary-magnet recesses between said first position and said second position.

22. A method of clearing obstructions, comprising:

translating a shuttle disposed outside a tube along a length thereof to correspondingly translate an elongate guide member that is at least partially disposed within said tube and magnetically coupled to said shuttle through a wall of said tube, wherein a magnetic field emanating from the shuttle is aligned substantially perpendicular to a longitudinal axis of said tube when viewed from a side thereof; and adjusting an amount of translational force available to translate a clearance member affixed to or formed with said elongate guide member within the tube by adjusting a position of a first magnetic element disposed within the shuttle;

wherein the position of said first magnetic element being dynamically adjustable between a first position remote from the tube and a second position proximate the tube when the shuttle is translated along said tube.

23. A device for clearing obstructions, comprising:

a shuttle defining a tube passage configured to accommodate a tube therein and adapted to translate along a length of said tube when accommodated in said tube passage; and a first primary magnetic element that is adjustable between a first position remote from the tube and a second position proximate the tube in order to adjust a coupling strength between the first primary magnetic element and a magnetic guide disposed within said tube when received through said tube passage.

* * * * *